United States Patent
Marion et al.

(10) Patent No.: US 11,332,503 B2
(45) Date of Patent: May 17, 2022

(54) PEPTIDES FOR TREATMENT AND PREVENTION OF HYPERGLYCAEMIA

(71) Applicants: UNIVERSITE DE STRASBOURG, Strasbourg (FR); INSERM (INSTITUT NATIONAL DE LA SANTÉ ET DE LA RECHERCHE MÉDICALE), Paris (FR); VAXINE PTY LTD, Adelaide (AU)

(72) Inventors: Vincent Marion, Lipsheim (FR); Nikolai Petrovsky, Adelaide (AU)

(73) Assignees: UNIVERSITE DE STRASBOURG, Strasbourg (FR); INSERM (INSTITUT NATIONAL DE LA SANTÉ ET DE LA RECHERCHE MÉDICALE), Paris (FR); VAXINE PTY LTD, Adelaide (AU)

( * ) Notice: Subject to any disclaimer, the term of this patent is extended or adjusted under 35 U.S.C. 154(b) by 0 days.

(21) Appl. No.: 16/627,389

(22) PCT Filed: Jun. 29, 2018

(86) PCT No.: PCT/EP2018/067657
§ 371 (c)(1),
(2) Date: Dec. 30, 2019

(87) PCT Pub. No.: WO2019/002583
PCT Pub. Date: Jan. 3, 2019

(65) Prior Publication Data
US 2020/0216504 A1    Jul. 9, 2020

(30) Foreign Application Priority Data
Jun. 30, 2017  (EP) .................. 17305843

(51) Int. Cl.
| | |
|---|---|
| C07K 14/47 | (2006.01) |
| C07K 7/06 | (2006.01) |
| C07K 7/08 | (2006.01) |
| A61K 38/00 | (2006.01) |
| A61K 45/06 | (2006.01) |
| A61P 3/10 | (2006.01) |
| C12N 9/12 | (2006.01) |

(52) U.S. Cl.
CPC ............. *C07K 14/47* (2013.01); *A61P 3/10* (2018.01); *C07K 7/06* (2013.01); *C07K 7/08* (2013.01); *C12N 9/12* (2013.01); *A61K 38/00* (2013.01); *A61K 45/06* (2013.01); *C07K 2319/00* (2013.01); *C12Y 207/11013* (2013.01)

(58) Field of Classification Search
None
See application file for complete search history.

(56) References Cited

U.S. PATENT DOCUMENTS

| | | |
|---|---|---|
| 4,946,778 A | 8/1990 | Ladner et al. |
| 6,225,120 B1 | 5/2001 | Ruvkun et al. |
| 6,605,713 B1 | 8/2003 | Furste et al. |
| 7,727,958 B2 | 6/2010 | Li |
| 8,686,115 B2 | 4/2014 | Cho |
| 10,821,159 B2 | 11/2020 | Marion et al. |
| 2002/0162127 A1 | 10/2002 | Gu et al. |
| 2005/0214757 A1 | 9/2005 | Wilson et al. |
| 2005/0250719 A1 | 11/2005 | Menne et al. |
| 2006/0067926 A1 | 3/2006 | Boylan et al. |
| 2008/0009025 A1 | 1/2008 | Alessi et al. |
| 2009/0081786 A1 | 3/2009 | Kheifets et al. |
| 2009/0191194 A1 | 7/2009 | Menne et al. |
| 2010/0216701 A1 | 8/2010 | Shafrir et al. |
| 2012/0225447 A1 | 9/2012 | Cho |
| 2012/0232037 A1 | 9/2012 | Farese |
| 2013/0331374 A1 | 12/2013 | Singh et al. |
| 2013/0336952 A1 | 12/2013 | Braiman-Wiksman et al. |
| 2017/0000857 A1 | 1/2017 | Marion et al. |
| 2020/0368314 A1 | 11/2020 | Marion et al. |
| 2021/0069301 A1 | 3/2021 | Marion et al. |
| 2021/0087230 A1 | 3/2021 | Marion |

FOREIGN PATENT DOCUMENTS

| | | |
|---|---|---|
| WO | WO 98/08856 | 3/1998 |
| WO | WO 03/034072 | 4/2003 |
| WO | WO 2004/028516 | 4/2004 |
| WO | WO 2005/010174 * | 2/2005 |
| WO | WO 2005/079300 | 9/2005 |
| WO | WO 2007/146981 | 12/2007 |
| WO | WO 2010/011313 | 1/2010 |
| WO | WO 2010/033617 | 3/2010 |
| WO | WO 2012/117245 | 9/2012 |
| WO | WO 2012/174489 | 12/2012 |
| WO | WO 2015/114062 * | 8/2015 |
| WO | WO 2019/025620 | 2/2019 |
| WO | WO 2019/115812 | 6/2019 |

OTHER PUBLICATIONS

Colas et al. (Nature. Apr. 11, 1996;380(6574):548-50) (Year: 1996).*
Database EBI Accession No. ADW81261, "AMPK modulating compound-related human PKCalpha peptide #129" Apr. 21, 2005, p. 1, XP002776351.
Written Opinion in International Application No. PCT/EP2018/067657, dated Sep. 11, 2018, pp. 1-6.
Collin, G.B. et al. "Mutations in ALMS1 cause obesity, type 2 diabetes and neurosensory degeneration in Alström syndrome" *Nature Genetics*, May 1, 2002, pp. 74-78, vol. 31, No. 1.
Written Opinion in International Application No. PCT/EP2015/051856, dated May 29, 2015, pp. 1-10.
Colas, et al., "Genetic selection of peptide aptamers that recognize and inhibit cyclin-dependent kinase 2," *Nature*, Apr. 11, 1996, pp. 548-550, vol. 380.
Cole, et al., "The EBV-hybridoma technique and its application to human lung cancer," *Monoclonal Antibodies and Cancer Therapy*, Jan. 1985, pp. 77-96, vol. 27.

(Continued)

*Primary Examiner* — Sergio Coffa
(74) *Attorney, Agent, or Firm* — Saliwanchik, Lloyd & Eisenschenk

(57) ABSTRACT

The present invention relates to peptides for the treatment or prevention of diabetes mellitus and associated disorders.

6 Claims, 12 Drawing Sheets

Specification includes a Sequence Listing.

(56) References Cited

OTHER PUBLICATIONS

International Preliminary Report on Patentability in International Application No. PCT/EP2015/051856 dated Aug. 2, 2016 (11 pages).
International Search Report and Written Opinion in International Application No. PCT/EP/051856 dated May 29, 2015 (15 pages).
Jayasena, et al., "Aptamers: An Emerging Class of Molecules That Rival Antibodies in Diagnostics," *Clinical Chemistry*, 1999, pp. 1628-1650, vol. 45, No. 9.
Kohler, et al., "Continuous cultures of fused cells secreting antibody of predefined specificity," *Nature*, Aug. 7, 1975, pp. 495-497, vol. 256.
Kozbor, et al., "The production of monoclonal antibodies from human lymphocytes." *Immunology Today*, Mar. 1983, pp. 72-79, vol. 4, Issue 3.
Marks, et al., "By-Passing Immunization: Building High Affinity Human Antibodies by Chain Shuffling," *Nature Biotechnology*, Jul. 1992, pp. 779-783, vol. 10.
Matsushita, et al., "Protein transduction technology," *Journal of Molecular Medicine*, May 2005, pp. 324-328, vol. 83, Issue 5.
Mccafferty, et al., "Phage antibodies: filamentous phage displaying antibody variable domains," *Nature*, Dec. 6, 1990, pp. 552-554, vol. 348.
Official Notification in EAPO Application No. 201691498 (PCT/EP2015/051856) dated Mar. 7, 2018 (with English translation) (7 pages).
Tuerk, et al., "Systematic evolution of ligands by exponential enrichment: RNA ligands to bacteriophage T 4 DNA polymerase," *Science*, Aug. 3, 1990, pp. 505-510, vol. 249, Issue 4968.
Verdine, et al., "Chapter one—Stapled Peptides for Intracellular Drug Targets," *Methods in Enzymology*, 2012, pp. 3-33, vol. 503.
Vives, et al., "Cell-penetrating and cell-targeting peptides in drug delivery," *Biochimic et Biophysica Acta-Reviews on Cancer*, Dec. 2008, pp. 126-138, vol. 1786, Issue 2.
Medkova et al., 1999, Interplay of C1 and C2 Domains of Protein Kinase C-alpha in Its Membrane Binding and Activation, *The Journal of Biological Chemistry*, 274(28): 19852-19861.

\* cited by examiner

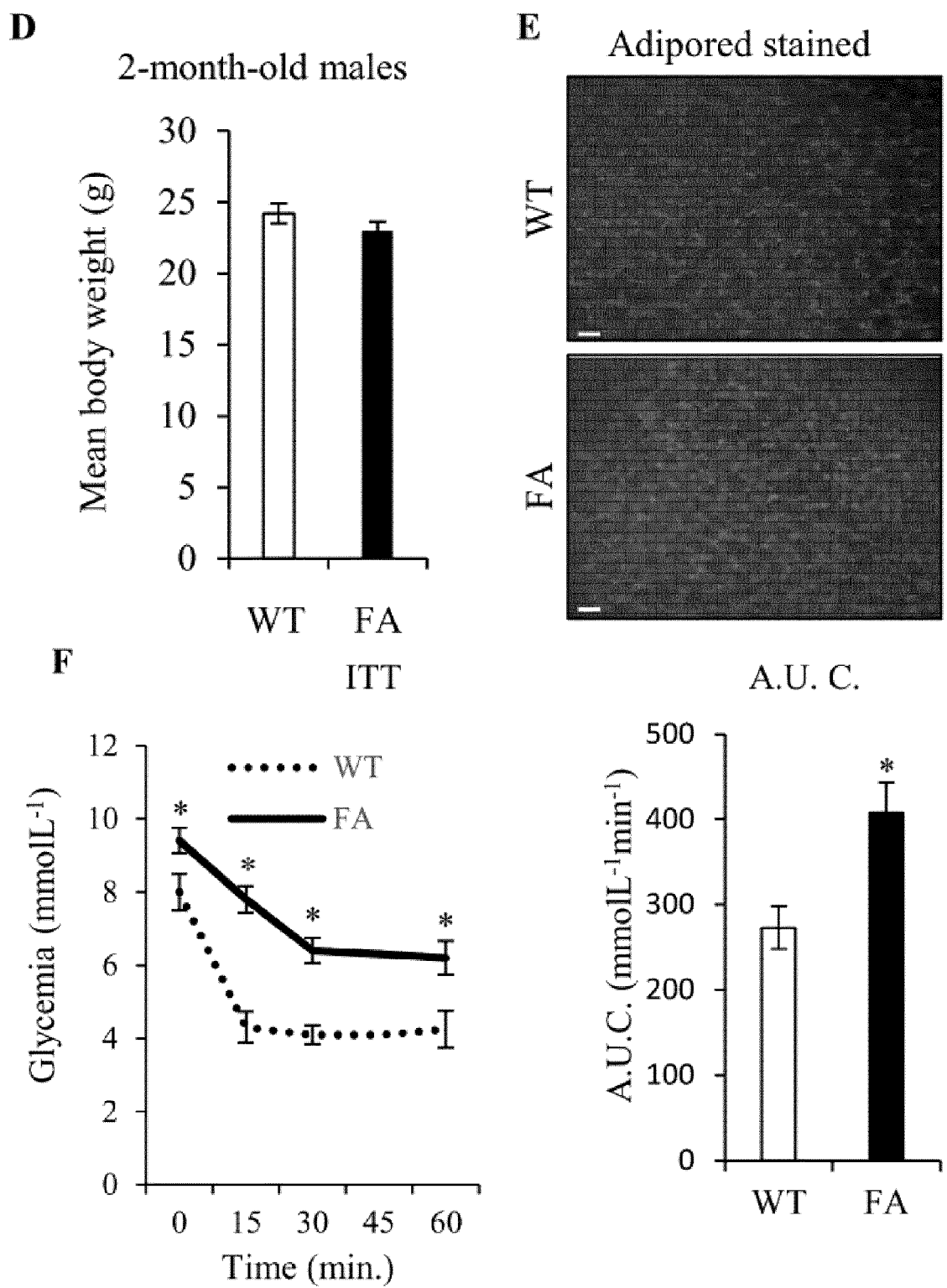
Figure 1 (following)

Figure 1 (following)

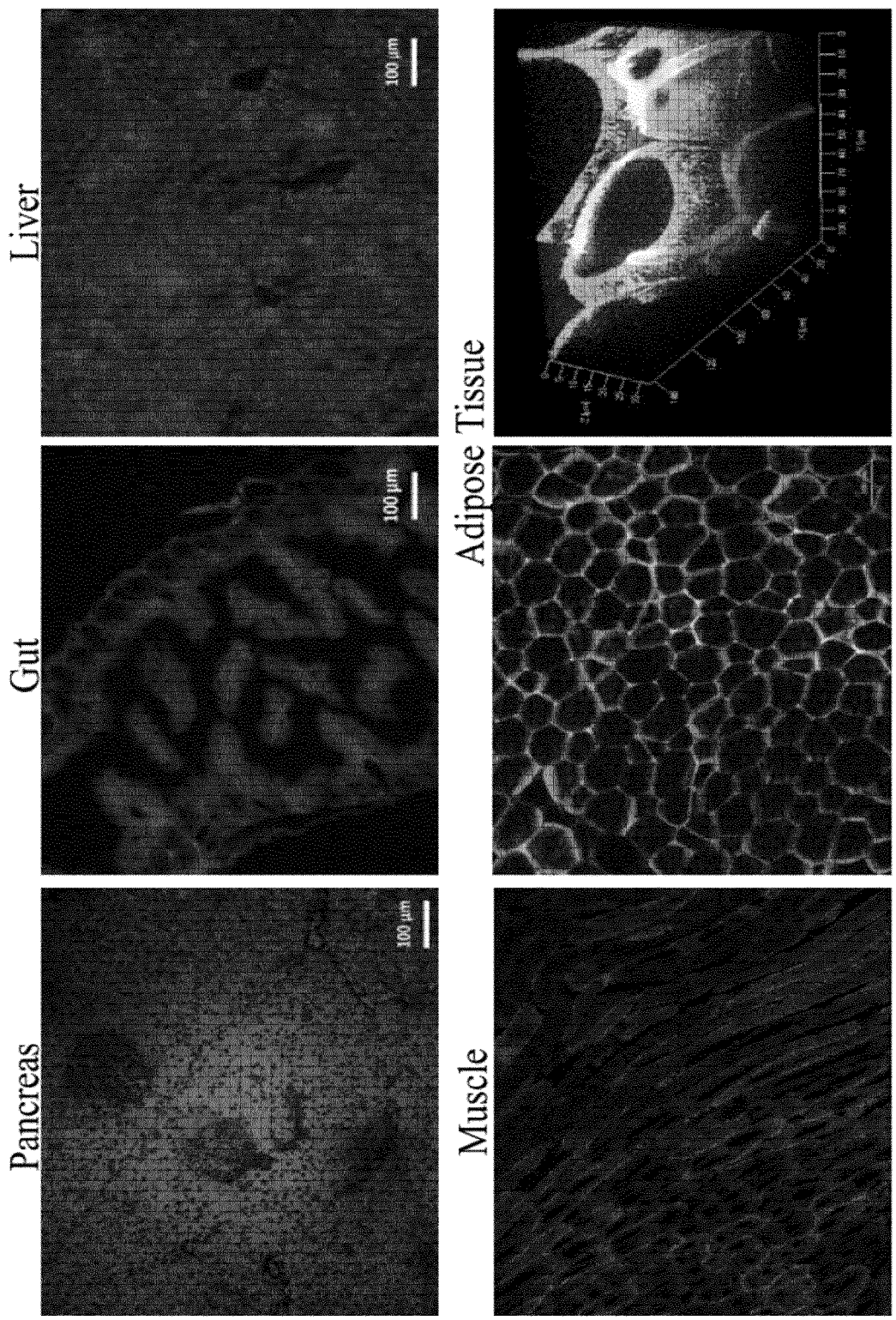
Figure 2 (following)

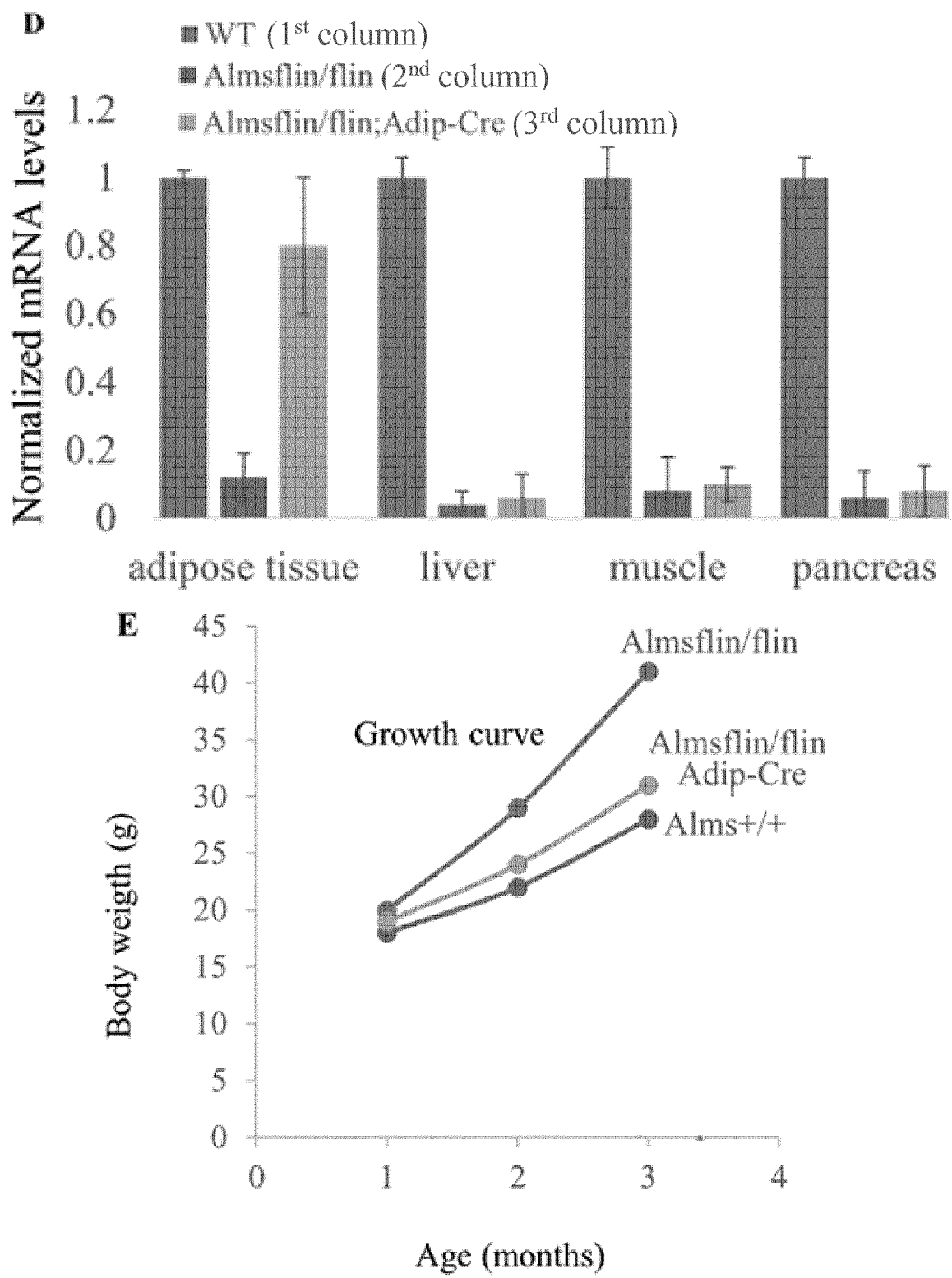
Figure 2 (following)

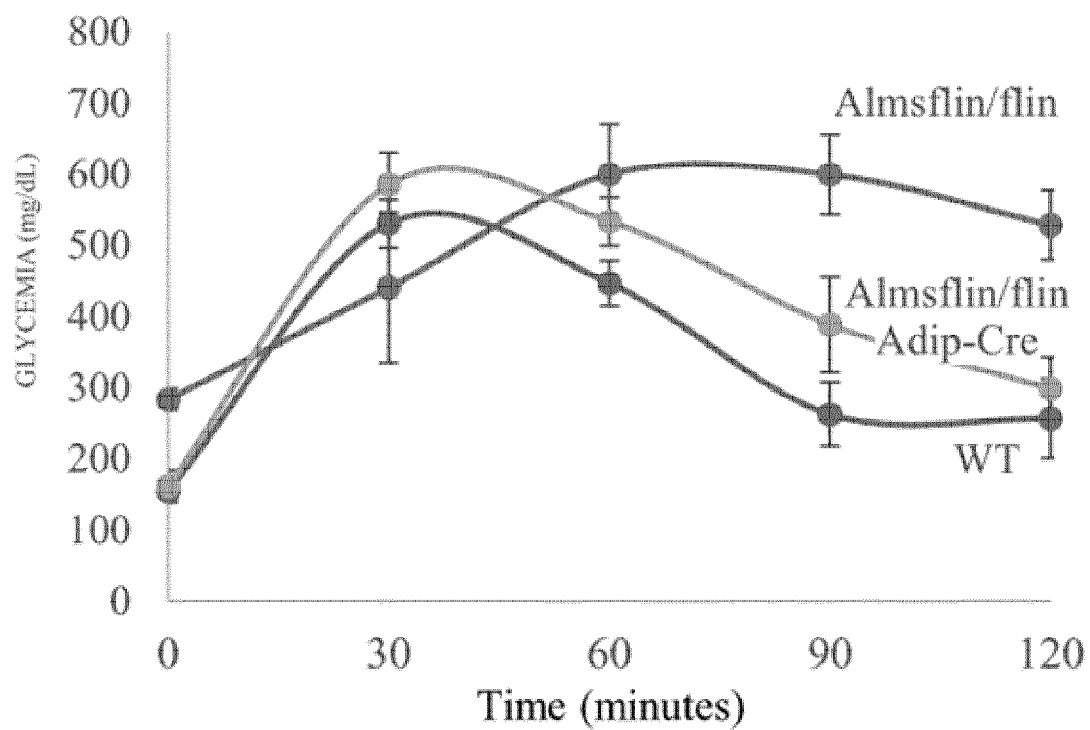
Figure 2 (following)

B

Potential PATAD peptide with MPR motif

```
         10         20         30         40         50
MADVFPGNDS TASQDVANRF ARKGALRQKN VHEVKDHKFI ARFFKQPTFC         C1 DOMAIN
         60         70         80         90        100
SHCTDFIWGF GKQGFQCQVC CFVVHKRCHE FVTFSCPGAD KGPDTDDPRS
        110        120        130        140        150
KHKFKIHTYG SPTFCDHCGS LLYGLIHQGM KCDTCDMNVH KQCVINVPSL
        160        170        180        190        200
CGMDHTE*KRG RIYLKAEVAD EKLHVTVRDA KNLIPMDPNG LSDPYVKLKL*       C2 domain
        210        220        230        240        250
*IPDPKNESKQ KTKTIRS*TLN PQWNESFTFK LKPSDKDRRL SVEIWDWDRT       Ca²⁺ binding domain
        260        270        280        290        300
TRNDFMGSLS FGVSELMKMP ASGWYKLLNQ EEGEYYNVPI PEGDEEGNME
        310        320        330        340        350
LRQKFEKAKL GPAGNKVISP SEDRKQPSNN LDRVKLTDFN *FLMVLGKGSF*       ATP binding domain:
        360        370        380        390        400                                GxGxG
G*KVML*ADRKG TEELYLAIKIL KKDVVIQDDD VECTMVEKR*V LALLDEPP*FL    Invariant lysine (K)
        410        420        430        440        450        *Kinase domain*
*TQLHSCFQTV DRLYFV***M***EYTNGGDLMYHIQ QVGKFKEPQA VFYAAEISIG    Gatekeeper residue (M)
        460        470        480        490        500
LFFLHKRGII YRDLKLDNVM LDSEGHIKI A *DFG***M***CKEHMM DGVTTRT*FCG   Invariant threonine
        510        520        530        540        550            Activation loop
T*P*DYIAPEII AYQPYGKSVD WWAYGVLLYE MLAGQPPFDG EDEDELFQSI
        560        570        580        590        600
MEHNVSYPKS LSKEAV SVCK GLMTKH*P*AKR LGCGPEGERD VREHAFFRRI
        610        620        630        640        650
DWEKLENREI QPPFKPKVCG KGAENFDKFF TRGQPVLTPP DQLVIANIDQ
        660        670
SDFEGFSYVN PQFVHPILQS AV
```

Figure 3 (following)

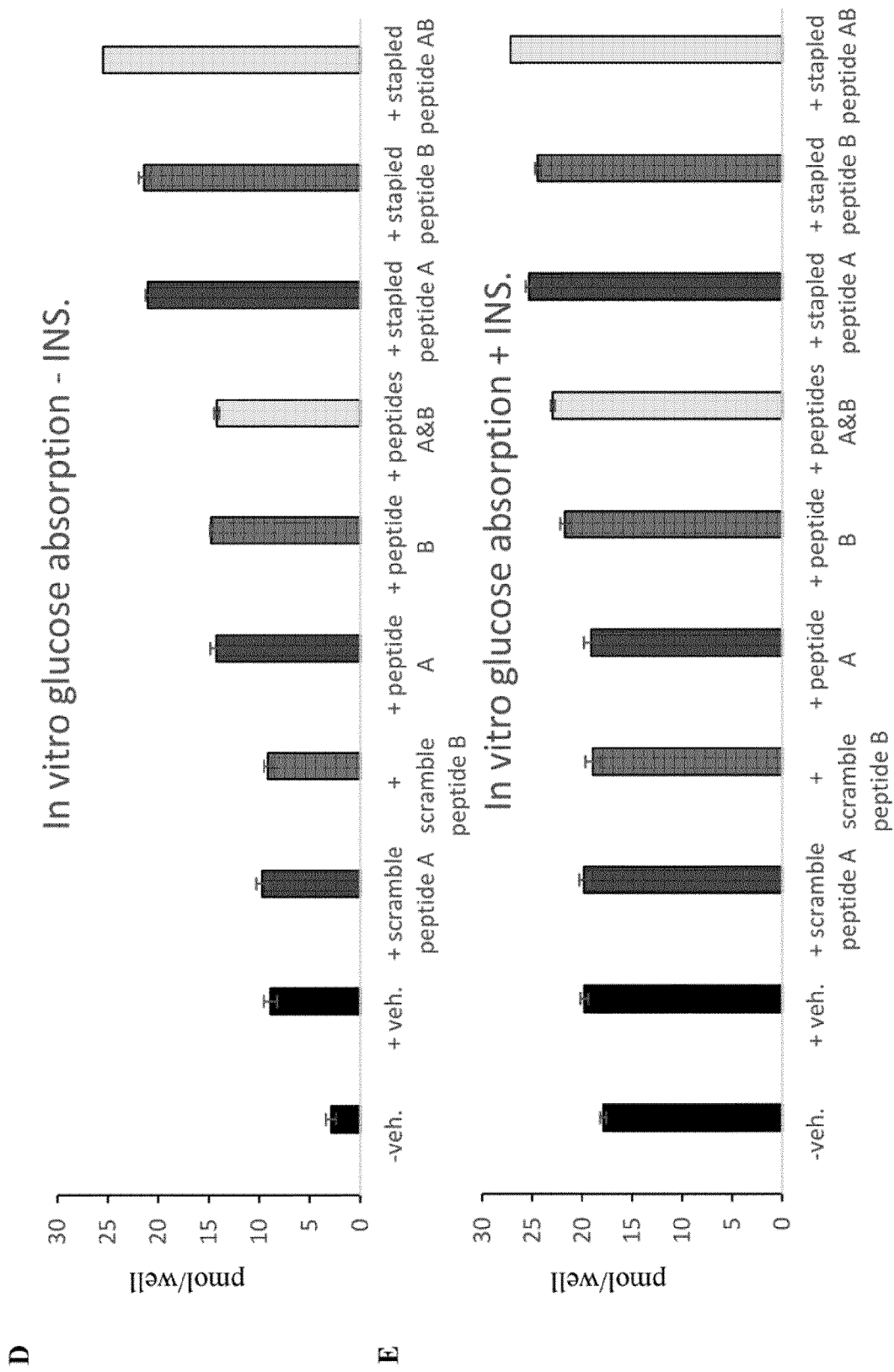
Figure 4 (following)

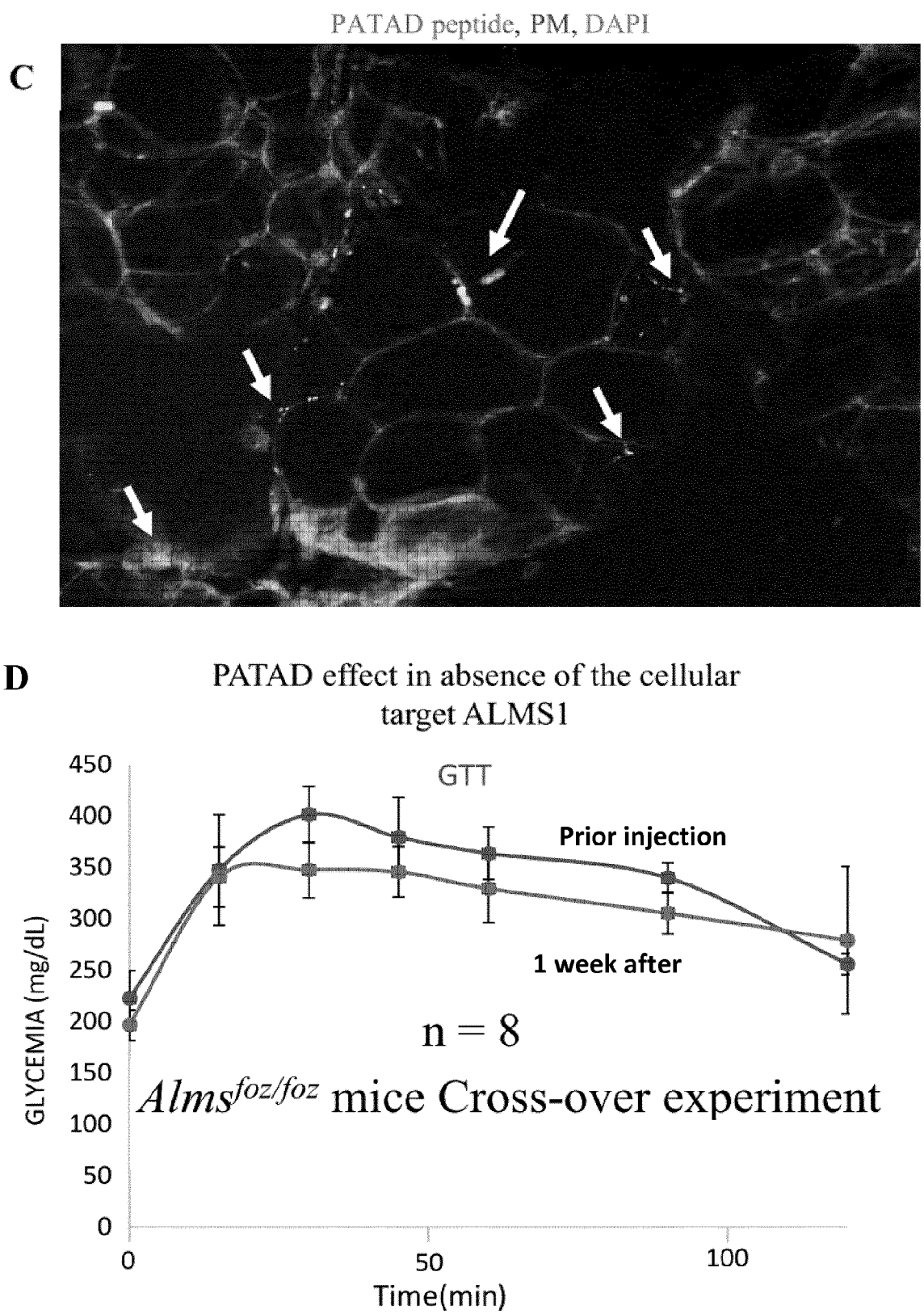
Figure 5 (following)

PEPTIDES FOR TREATMENT AND PREVENTION OF HYPERGLYCAEMIA

CROSS-REFERENCE TO RELATED APPLICATION

This application is the U.S. national stage application of International Patent Application No. PCT/EP2018/067657, filed Jun. 29, 2018.

The Sequence Listing for this application is labeled "Seq-List.txt" which was created on Nov. 22, 2019 and is 25 KB. The entire content of the sequence listing is incorporated herein by reference in its entirety.

FIELD OF THE INVENTION

The present invention relates to the field of the medicine. More particularly, it relates to treatment of diabetes mellitus.

BACKGROUND OF THE INVENTION

Diabetes mellitus (diabetes) is a group of metabolic diseases in which a person has high blood sugar, either because the pancreas does not produce enough insulin, or because cells do not respond to the insulin that is produced.
There are two main types of diabetes:
Type 1 results from the body's failure to produce insulin, and currently requires the person to inject insulin or wear an insulin pump.
Type 2 results from insulin resistance, a condition in which cells fail to respond properly to insulin.

Rates of type 2 diabetes have increased markedly since 1960 in parallel with obesity: As of 2014 there were globally approximately 422 million people with the disease compared to around 30 million in 1985. Long-term complications from diabetes include heart disease, stroke, diabetic retinopathy, chronic renal failure, peripheral vascular disease leading to amputations.

Unfortunately, existing diabetes treatments while they may reduce blood glucose levels in the short-term, generally fail to maintain normoglycaemia in the longer term, resulting in the need to progressively add more hypoglycaemic agents to a patient's treatment to try and maintain control of their blood sugar levels. Nevertheless, even when treated with multiple hypoglycaemic agents in combination many diabetic patients still do not achieve good glycaemic control. In addition, current hypoglycaemic agents such as sulphonylureas or insulin increase the risk of serious and even life-threatening hypoglycaemia, thereby increasing the difficulty of achieving ideal diabetic control using current treatments.

There is presently no single drug able to reverse all aspects of diabetes or prevent its progressive nature. The progressive nature of type 2 diabetes means that many patients will eventually require a combination of oral hypoglycaemic medication, possibly together with insulin and/or incretin-based injections. Anti-diabetic agents have been developed in order to counteract hyperglycaemia in type 2 diabetes acting to reduce insulin resistance (biguanides and thiazolidinediones) or enhance insulin secretion (sulfonylureas, glinides, dipeptidylpeptidase-4 inhibitors, glucagon-like peptide 1 receptor agonists). However, many of these medications have been shown to have deleterious side effects including hypoglycaemia, nausea, diarrhea, weight gain, peripheral edema, congestive heart failure, and osteoporotic fractures. There is also a major problem with a loss of effectiveness of current hypoglycaemic agents with long-term use. Thus, there is a need for alternative better medications for the treatment of diabetes and related conditions.

SUMMARY OF THE INVENTION

Even though the art teaches that adipose tissue is only responsible for disposal of less than 20% of daily glucose intake and production, the inventors have designed novel peptides that induce sustained insulin-independent glucose transport, and, surprisingly, provide sustained reduction in elevated glucose levels and other metabolic disturbances in diabetic individuals.

The novel and surprising discovery that induction of insulin-independent glucose uptake into adipocytes is able to reverse hyperglycaemia and its down-stream metabolic consequences, enables the design of novel diabetes therapies specifically targeting insulin-independent adipocyte glucose uptake. The inventors have designed the novel peptides of the present disclosure and shown that injection of these peptides into adipose tissue is able to restore normoglycaemia in diabetic individuals while not inducing hypoglycaemia or changing body weight.

Accordingly, the present invention relates to novel peptide compositions for the treatment or prevention of diabetes mellitus, insulin resistance, hyperlipidaemia, coronary artery disease, diabetic retinopathy, diabetic neuropathy, diabetic nephropathy, insulin resistance, hyperglycemia, obesity, lipodystrophy, insulin deficiency, beta cell dysfunction, hyperinsulinaemia or combinations thereof, in particular through induction of insulin-independent adipocyte glucose uptake.

In a first aspect, the present invention relates to one or more peptides that induces insulin-independent adipocyte glucose transport, wherein:
the peptide sequence comprises the sequence of a segment of a PKC (Protein Kinase C);
the peptide comprises at least one methionine, one proline and one arginine;
the peptide has a length of at least 8 amino acids and less than 40 amino acids, preferably a length of at least 10 amino acids and less than 30 amino acids, more preferably of at least 12 amino acids and less than 25 amino acids; and
the peptide sequence may comprise 1, 2, 3, 4, or 5 substitution(s), deletion(s), addition(s), or a mixture thereof within said sequence of a segment of a PKC.

In one embodiment, the peptide adopts an alpha helical conformation.

In another embodiment, the peptide is modified by a chemical cross-linking process such as stapling.

In still another embodiment, the peptide sequence comprises a sequence according to one of the following formulae: M-(X)m-P-(X)n-R or M-(X)m-R-(X)n-P or P-(X)m-M-(X)n-R or P-(X)m-R-(X)n-M or R-(X)m-P-(X)n-M or R-(X)m-M-(X)n-P, preferably M-(X)m-R-(X)n-P or P-(X)m-R-(X)n-M or R-(X)m-M-(X)n-P or M-(X)m-P-(X)n-R. In these sequences, X is any amino acid, m and n are integers from 1 to 20, preferably from 2 to 15, even more preferably from 2 to 7, and m+n is less than 30, preferably m+n is less than 20.

In one embodiment, said PKC is selected from the group consisting of an alpha-PKC (αPKC), a beta-PKC (βPKC) including βI and βII PKC, delta-PKC, theta-PKC, eta-PKC and epsilon-PKC, more preferably an αPKC of SEQ ID No 1.

In another embodiment, the peptide sequence comprises a sequence selected from the group consisting of MVEKRV- LALLDKP (SEQ ID No 2), PFLTQLHSCFQTVDR-LYFVM (SEQ ID No 3), RLYFVMEYVNGGDLMYHIQQVGKFKEP (SEQ ID No 4), MYHIQQVGK-FKEPQAVFYAAEISIGLFFLHKR (SEQ ID No 5), PQAVFYAAEISIGLFFLHKRGIIYRDLK-LDNVM (SEQ ID No 6), MDGVTTRTFCGTP (SEQ ID No 7), and MTKHPAKR (SEQ ID No 8), preferably from the group consisting of MVEKRVLALLDKP (SEQ ID No 2), PFLTQ-LHSCFQTVDRLYFVM (SEQ ID No 3), PQAVFYAAEISIGLFFLHKRGIIYRDLKLDNVM (SEQ ID No 6), MDGVTTRTFCGTP (SEQ ID No 7), and MTKHPAKR (SEQ ID No 8), even more preferably from the group consisting of MVEKRVLALLDKP (SEQ ID No 2), MDGVT-TRTFCGTP (SEQ ID No 7), and MTKHPAKR (SEQ ID No 8). Optionally, the peptide comprises 1, 2, 3, 4, or 5 substitution(s), deletion(s), addition(s), or a mixture thereof, preferably 1, 2, or 3 substitution(s).

In yet another embodiment, the peptide sequence comprises a sequence selected from the group consisting of VECTMVEKRVLALLDKPPFLTQLHS (SEQ ID No 9), MCKEHMMDGVTTRTFCGTPD (SEQ ID No 10), and SICKGLMTKHPAKRLGCGPEG (SEQ ID No 11), and optionally it comprises 1, 2, 3, 4, or 5 substitution(s), deletion(s), addition(s), or a mixture thereof, preferably 1, 2, or 3 substitution(s). In particular, the peptide sequence may consist in a sequence selected from the group consisting of VECTMVEKRVLALLDKPPFLTQLHS (SEQ ID No 9), MCKEHMMDGVTT-RTFCGTPD (SEQ ID No 10), and SICKGLMTKHPAKRLGCGPEG (SEQ ID No 11).

In still another embodiment, the peptide(s) of the present disclosure are modified by a chemical cross-linking process such as stapling, preferably the stapled peptide sequence consists of a sequence selected from the group consisting of VECTMVEKRVLALLDKPPFLTQLHS (SEQ ID No 9), MCKEHMMDGVTTRTFCGTPD (SEQ ID No 10), and SICKGLMTKHPAKRLGCGPEG (SEQ ID No 11), wherein the residues which are bold and underlined carry the stapling.

In a second aspect, the invention also relates to a pharmaceutical composition comprising the peptide(s) of the present disclosure. It also relates to a peptide of the present disclosure for use as a drug.

In a third aspect, the invention relates to peptide(s) according to the present disclosure or to a pharmaceutical composition according to the present disclosure, for use in treating or delaying the progression or onset of diabetes mellitus, insulin resistance, hyperlipidaemia, coronary heart disease, diabetic retinopathy, diabetic neuropathy, diabetic nephropathy, insulin resistance, hyperglycemia, obesity, lipodystrophy, insulin deficiency, beta cell dysfunction or hyperinsulinaemia and preferably in treating or delaying the progression or onset of type 2 diabetes mellitus.

In one embodiment, the peptide(s) of the present disclosure or the pharmaceutical composition according to the present disclosure, is used in combination with another anti-diabetic or weight loss agent, preferably selected from the group consisting of insulin, metformin, sulfonylureas such as tolbutamide, acetohexamide, tolazamide, chlorpropamide, glyburide (also called glibenclamide), glimepiride, glipizide, glicazide, glycopyramide and gliquidone, alpha-glucosidase inhibitors such as acarbose, miglitol and voglibose, thiazolidinediones such as pioglitazone and rosiglitazone, meglitinides such as repaglinide and nateglinide, incretin mimetics, glucagon-like peptide analogs and agonists such as exenotide, taspoglutide and liraglutide, dipeptidyl peptidase-4 inhibitors such as vildagliptin, sitagliptin, saxagliptin, linagliptin, alogliptin, and septagliptin, amylin analogs such as pamlintide, glycosurics such as canagliflozin, dapagliflozin and empagliflozin, or any combination thereof.

In some embodiments, the peptide of the present technology comprises an amino acid sequence selected from the group consisting of H-VECTM-R8-EKRVLA-S5-LDKPP-FLTQLHS-OH (SEQ ID NO: 21); H-VECTM-R8-EKRVLA-S5-LDKPPFLTQLHS-NH2 (SEQ ID NO: 22); H-CTM-R8-EKRVLA-S5-LDKPPFLTQLHS-OH (SEQ ID NO: 23); H-M-R8-EKRVLA-S5-LDKPPFLTQLHS-OH (SEQ ID NO: 24); Cbz-R8-EKRVLA-S5-LDKPP-FLTQLHS-OH (SEQ ID NO: 25); H-VECTM-R8-EKRVLA-S5-LDKPPFLTQL-OH (SEQ ID NO: 26); H-VECTM-R8-EKRVLA-S5-LDKPPFLT-OH (SEQ ID NO: 27); H-VECTM-R8-EKRVLA-S5-LDKPPF-OH (SEQ ID NO: 28); H-VECTM-R8-EKRVLA-S5-LDKP-OH (SEQ ID NO: 29); H-VECTM-R8-EKRVLA-S5-LD-OH (SEQ ID NO: 30); H-VE(AAB)TM-R8-EKRVLA-S5-LDKPP-FLTQLHS-OH (SEQ ID NO: 31); H-VECT(AAH)-R8-EKRVLA-S5-LDKPPFLTQLHS-OH (SEQ ID NO: 32); H-VE(AAB)T(AAH)-R8-EKRVLA-S5-LDKPPFLTQLHS-OH (SEQ ID NO: 33); H-VECTM-R8-EKRVLA-S5-LDKPPFLTQLHS-OH hydrogenated (SEQ ID NO: 34); H-VECTM-S5-EKR-S5-LALLDKPPFLTQLHS-OH (SEQ ID NO: 35); and H-LPHET-R8-RLSQKV-S5-TKLD-CLMFVEPA-OH (SEQ ID NO: 36).

For stapled peptides described herein, stapling is positioned on the R8 and S5 residues.

(E) Growth curve for the male mice with the indicated genotype showing Alms1$^{ftin/ftin}$ becoming obese.

(F) Glucose tolerance tests in male mice with the indicated genotype depicting that the Alms$^{ftin/ftin}$ are glucose intolerant but restoring ALMS1 only in the adipose tissue is enough to restore glucose tolerance.

Figure 3:
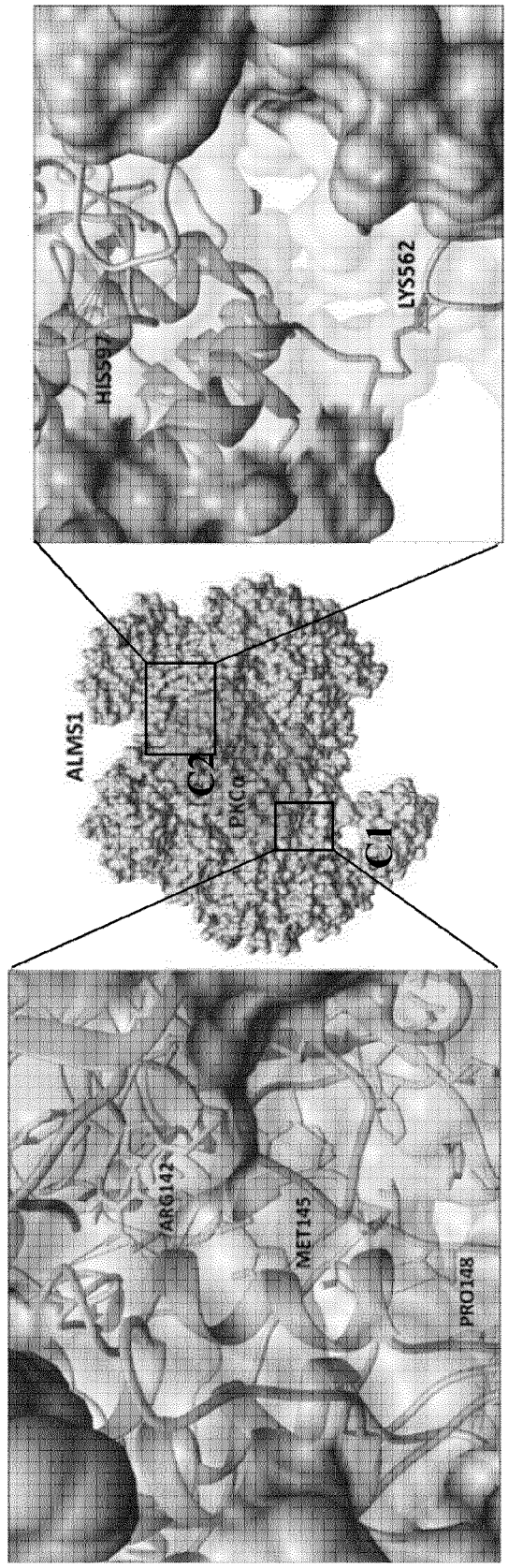

FIG. 3: In silico modelling of ALMS1 and αPKC binding with the identification of the potential peptides from the human αPKC isoform.

(A): In silico modelling of ALMS1 and αPKC binding with the identification of three key amino acids: Arginine, Methionine and Proline.

(B) Identification of potential peptides from the human αPKC isoform sequence (SEQ ID NO: 37). These peptides may be referred to PATAD peptides standing for Peptide of APKC Targeting ALMS for Diabetes.

Figure 4:
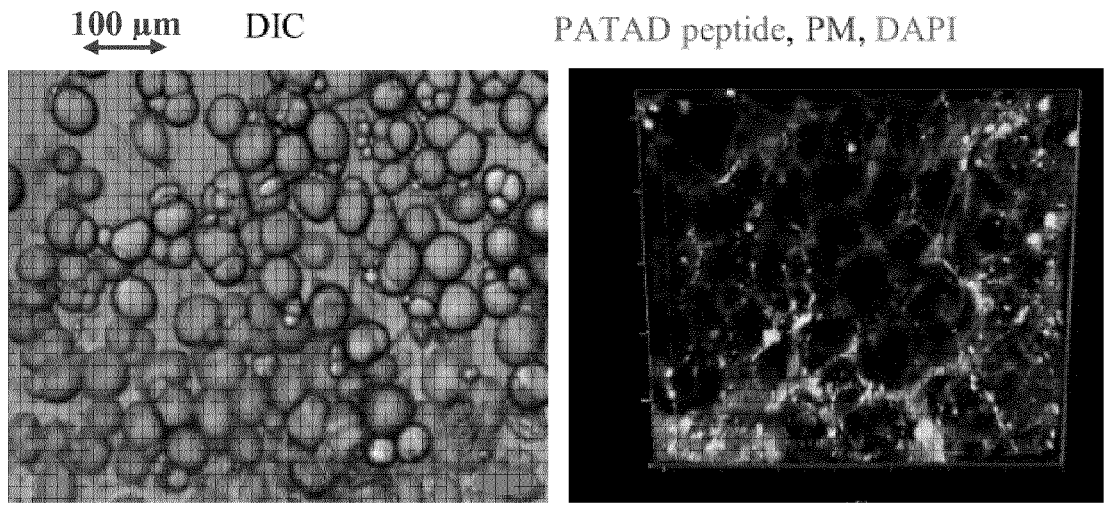
Figure 4:
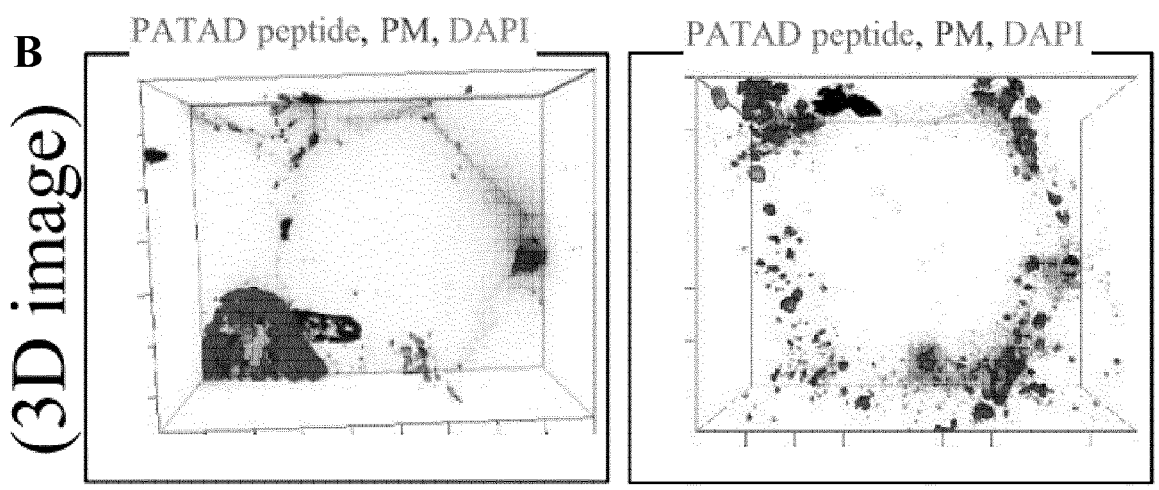
Figure 4:
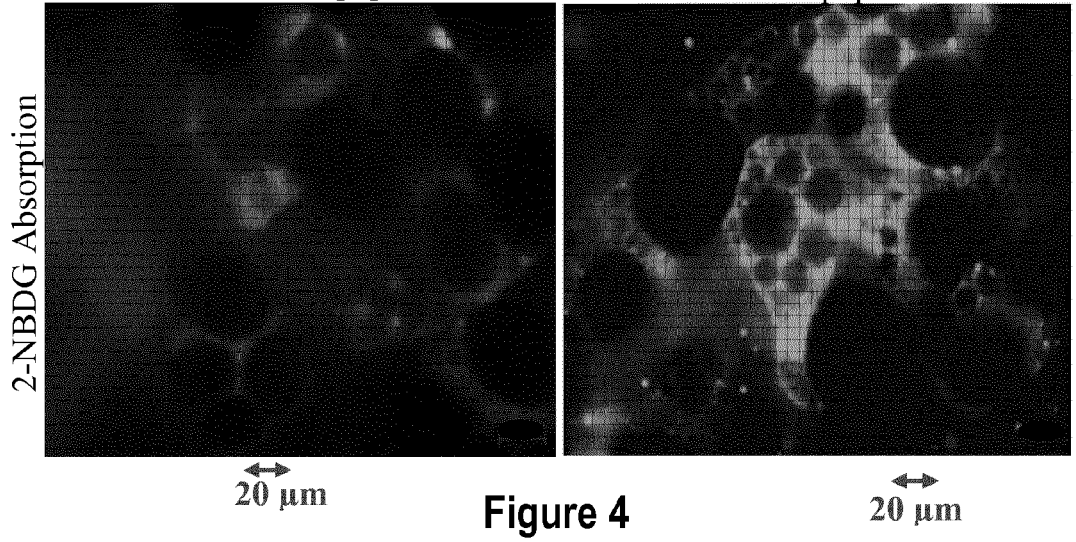

FIG. 4: In vitro characterization of two peptides for their glucose absorption triggering capacity.

(A) Representative picture depicting the cellular entry assessment of the mixture of FAM-labelled stapled peptides A (SEQ ID No 9) and B (SEQ ID No 11) in human adipocytes. DIC: Differential interference contrast mode for living cell acquisition in left panel. In right panel, fluorescent detection of the FAM-labelled peptide with the labelled plasma membrane (PM).

(B) 3D images of the cellular uptake of PATAD peptides identified in FIG. 3; either peptide A (left panel) or peptide B (right panel) treated adipocyte showing the spots inside the peptide inside the adipocyte.

(C) Photographs showing absorption of 2-NBDG in absence of INS in adipocytes following treatment with a combination of the stapled peptides A and B.

(D) Quantification of intracellular glucose analogue 2-NB in absence of INS in adipocytes following the indicated peptide treatment (n=8 per group).

(E) Quantification of intracellular glucose analogue 2-NB in presence of INS in adipocytes following the indicated peptide treatment (n=8 per group).

Figure 5:
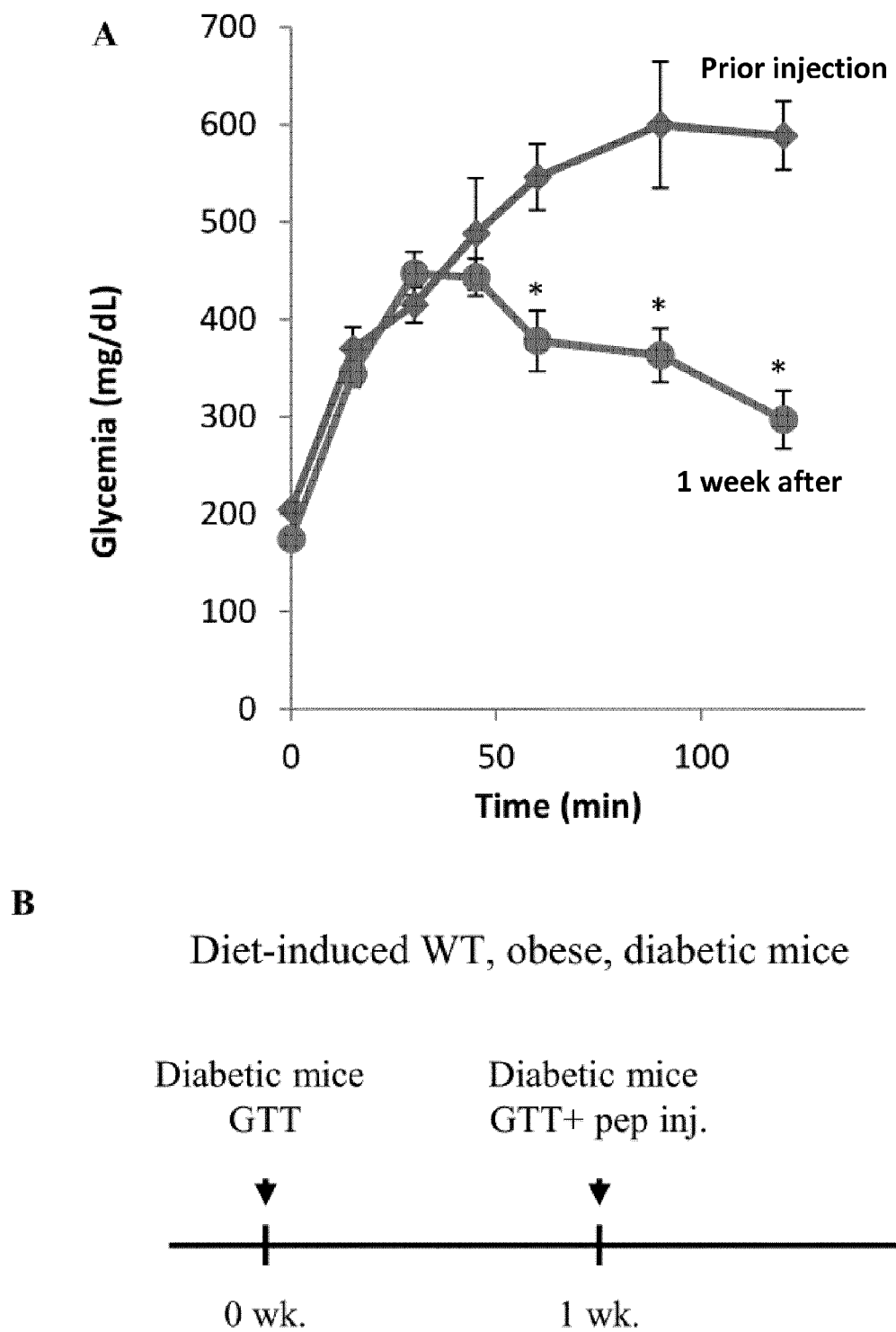

FIG. 5: Adipose tissue related endocrine aspects and their systemic impacts (A) Glucose tolerance test (GTT) in diet induced obese (DIO) and diabetic mice prior to subcutaneous injection with a combination of the stapled peptides A and B and 1 week later following peptide injection.

(B) Schematic representation of the experimental set-up for the peptide treatment in the DIO mice.

(C) Fluorescent detection of the FAM-labelled peptides A and B (pointed by arrows) with the labelled plasma membrane (PM) inside the adipose tissue obtained from the site of injection.

(D) GTT in Almsfoz/foz mice lacking functional ALMS1 prior to injection with a combination of the stapled peptides A and B and 1 week later after peptides subcutaneous injection.

DETAILED DESCRIPTION OF THE INVENTION

Surprisingly, even though the art teaches that adipose tissue is only responsible for disposal of less than 20% of daily glucose intake and production, the inventors have found that induction of insulin-independent adipocyte glucose uptake is of itself able to restore normoglycaemia and correct downstream metabolic defects in obese diabetic individuals. The novel and surprising discovery that simple induction of insulin-independent glucose uptake into adipocytes is able to reverse whole body obesity-associated hyperglycaemia and its down-stream metabolic consequences, allows the design of novel diabetes therapies specifically targeting insulin-independent adipocyte glucose uptake. The inventors have subsequently designed the novel peptides of the present disclosure and despite their target, Alms1, being an intracellular protein have shown surprisingly that injection of these peptides into adipose tissue is able to restore normoglycaemia in diabetic individuals while not inducing hypoglycaemia or changing body weight.

Accordingly, the invention relates to a method for the treatment or prevention of hyperglycaemia, through induction of insulin-independent adipocyte glucose uptake.

Definitions

ALMS1, Alström syndrome protein 1, is a protein encoded by the ALMS1 gene. Mutations in the ALMS1 gene have been found to be causative for Alström syndrome. It is described in several databases, namely UniProt ID No Q8TCU4; Gene ID No 7840, HGNG ID No 428. Reference sequences are disclosed in Genbank under NM_015120.4 for mRNA and NP_055935.4 for protein.

TBC1D4 (TBC1 domain family member 4), also currently called As160, is supposed to act as a GTPase-activating protein for RAB2A, RAB8A, RAB10 and RAB14. It is described in several databases, namely UniProt ID No O60343, Gene ID No 9882, HGNG ID No 19165. Reference sequences are disclosed in Genbank under NM_014832.3 for mRNA and NP_055647.2 for protein (for isoform 1, chosen as canonical sequences). The isoform 2, which differs from isoform 1 by the missing of the amino acids in positions 678-740 and referenced in UniProt under No O60343-2, promotes insulin-induced glucose transporter SLC2A4/GLUT4 translocation at the plasma membrane, thus increasing glucose uptake.

The terms "Protein kinase C" and "PKC" (EC 2.7.11.13) are equivalent and refers to a family of protein kinase enzymes that are involved in controlling the function of other proteins through the phosphorylation of hydroxyl groups of serine and threonine amino acid residues on these proteins. PKC are typically activated by signals such as increases in the concentration of diacylglycerol (DAG) or calcium ions (Ca2+). PKC play important roles in several signal transduction cascades.

The PKC family comprises at least fifteen isozymes in humans, divided into three main subfamilies, conventional (or classical) PKCs, novel PKCs, and atypical PKCs.

Conventional (c)PKCs comprises the isoforms α, βI, βII, and γ. These PKCs require $Ca^{2+}$, DAG, and a phospholipid such as phosphatidylserine for activation.

Novel (n)PKCs include the ϵ, ε, η, and θ isoforms. These PKCs require DAG, but do not require Ca2+ for activation.

Atypical (a)PKCs include the ζ, ι, and λ isoforms. These PKCs require neither Ca2+ nor diacylglycerol for activation.

Protein kinase C alpha type, also called αPKC, PKC-A or PKC-alpha, belongs to a family of serine- and threonine-specific protein kinases that can be activated by calcium and the second messenger diacylglycerol. It is described in several databases, namely UniProt ID No P17252, Gene ID No 9393, HGNG ID No 5578. Reference sequences are disclosed in Genbank under NM_02737.2 for mRNA and NP_002728.1 for protein. The protein sequence of human αPKC is disclosed in SEQ ID No 1.

"consists of," "consists essentially of" or "substantially comprises": The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context. For instance, a peptide or protein described herein as comprising a particular sequence should be understood as also describing a peptide or protein consisting of that sequence, unless otherwise stated or clearly contradicted by context. By "consists essentially of" is intended that the peptide or protein consists of that sequence, but it may also include 1, 2, 3, 4, 5, 6, 7, 8, 9 or 10 substitutions, additions, deletions or a mixture thereof, preferably 1, 2, 3, 4, or 5 substitutions, additions, deletions or a mixture thereof. In particular, by "essentially consist in", it may be intended that the peptide may include 1, 2, 3, 4, 5, 6, 7, 8, 9 or 10 additional amino acids at the N and/or C-terminal end, preferably 1, 2, 3, 4, or 5 additional amino acids, and/or 1, 2 or 3 substitutions, deletions, additions, or a mixture thereof.

As used herein, the term "substitution" refers to the exchange of a single amino-acid by another in a peptide sequence.

As used herein, the term "deletion" refers to the removal of a single amino-acid in a peptide sequence.

As used herein, the term "insertion" or "addition" are equivalent and refer to the addition of a single amino-acid in a peptide sequence.

In the peptide sequences disclosed herein, the amino acids are represented by their one letter code according to the following nomenclature: A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophane and Y: tyrosine.

As used herein, the terms "sequence identity" or "identity" refers to an exact amino acid to amino acid correspondence of two peptides. Percent of identity can be determined by a direct comparison of the sequence information between two molecules by aligning the sequences, counting the exact number of matches between the two aligned sequences, dividing by the length of the shorter sequence, and multiplying the result by 100.

The sequence identity can be determined by alignment of two peptide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity. GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths.

By "increased", "increase" or "enhance" is intended to refer to a measurement increased by at least 10, 20, 30, 40, 50, 60, 70, 80 or 90% when compared to the measurement measured in absence of the tested molecule in the same conditions. By "decreased" or "decrease" is intended to refer to a measurement decreased by at least 10, 20, 30, 40, 50, 60, 70, 80 or 90% when compared to the measurement measured in absence of the tested molecule in the same conditions.

As used herein, the term "treatment", "treat" or "treating" refers to any act intended to ameliorate the health status of patients, such as cure, alleviate or delay of the disease. It includes preventive as well as therapeutic treatment. The term treatment designates in particular the correction, retardation, or reduction of an impaired glucose homeostasis. The term "treatment" also designates an improvement in glucose uptake (e.g., capture of glucose by adipocytes) or reversal of any negative effect of raised blood glucose or insulin resistance. Within the context of the invention, the terms "controlling the blood glucose level" or "the control of blood glucose level" refer to the normalization or the regulation of the blood or plasma glucose level in a mammalian subject having abnormal levels (i.e., levels that are below or above a known reference, median, or average value for a corresponding mammalian subject with a normal glucose homeostasis).

As used herein, the term "effective amount" refers to a quantity of a peptide of the present disclosure or of a pharmaceutical composition of the present disclosure which treats or delays the progression or onset of diabetes mellitus, insulin resistance, hyperlipidaemia, coronary heart disease, diabetic retinopathy, diabetic neuropathy, diabetic nephropathy, insulin resistance, hyperglycemia, obesity, lipodystrophy, insulin deficiency, beta cell dysfunction or hyperinsulinaemia, preferably diabetes mellitus, even more preferably type 2 diabetes mellitus.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient, such as a peptide of the present disclosure, or by a pharmaceutical composition according to the present disclosure, capable to treat or to delay the progression or onset of diabetes mellitus, insulin resistance, hyperlipidaemia, coronary heart disease, diabetic retinopathy, diabetic neuropathy, diabetic nephropathy, insulin resistance, hyperglycemia, obesity, lipodystrophy, insulin deficiency, beta cell dysfunction or hyperinsulinaemia, preferably diabetes mellitus, even more preferably type 2 diabetes mellitus.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the actives ingredients.

As used herein, the terms "subject", "individual" or "patient" are interchangeable and refer to an animal, preferably to a mammal, even more preferably to a human, including adult, child, newborn and human at the prenatal stage.

In the present document, the term «about» refers to a range of values of ±10% of the specified value. For example, «about 50» comprise values of ±10% of 50, i.e. values in the range between 45 and 55. Preferably, the term «about» refers to a range of values of ±5% of the specified value.

Peptides

The peptide(s) according to the present disclosure induces insulin-independent glucose uptake into adipocytes, thereby being able to restore normoglycaemia in diabetic individuals or improve glycaemia in diabetic individuals.

The peptide according to the present disclosure comprises at least one methionine, one proline and one arginine.

In one aspect, the peptide of the present disclosure has an alpha helix structure. As used herein, the terms "alpha helix" "α-helix", "classic Pauling-Corey-Branson α-helix" and "3.6$_{13}$-helix" are equivalent and refer to each other. The term "alpha helix" refers to a common motif in the secondary structure of proteins which is a right hand-coiled or spiral conformation (helix) in which every backbone N—H group donates a hydrogen bond to the backbone C=O group of the amino acid located three or four residues earlier along the protein sequence. An alpha helix has an average number of residues per helical turn of about 3.6 residues and 13 atoms are involved in the ring formed by the hydrogen bond.

In a particular embodiment, the peptide of the present disclosure has an alpha helix structure and/or has a sequence which is predictive of an alpha helix structure. Methods to determine the structure of a peptide are well known from the man skilled in the art, such as Circular Dichroism or NMR. Likewise, methods to predict an alpha helix structure of a peptide are well known from the man skilled in the art such as STRIDE (Frishman D., Argos P., Proteins, vol. 23, no 4, 1995, p. 566-579); DEFINE (Richards F. M., Kundrot C. E., Proteins, vol. 3, no 2, 1988, p. 71-84); DSSP (Touw et al. Nucleic Acids Research 2015; 43: D364-D368; Kabsch & Sander. Biopolymers. 1983, 22, 2577-2637).

In another particular embodiment, the peptide according to the present disclosure is designed or modified in order to maintain it in an alpha helical conformation. As known in the art, this can be achieved via a variety of methods, including modification of the amino acid sequence with substitution of amino acids not critical for biological effects, use of non-natural amino acids, peptide cyclization, and modifications to the peptide backbone or addition of chemical links between amino acids in the peptide chain. Such modifications can be made to peptides, for example, to increase their thermal and protease stability.

In particular, the peptide of the present disclosure is modified by a chemical cross-link. For instance, the peptide can be a stapled peptide. In one embodiment, the peptide of the present disclosure is stapled. The term "stapled peptide" or "stitched peptide", as used herein, refers to an artificially modified peptide in which the peptide secondary structure is stabilized with one or more artificial molecular crosslinks (bridges) that connect adjacent turns of α-helices in the peptide. The methods for preparing stapled peptides are well known in the art, for instance in Verdine & Hilinski (2012, Methods Enzymol, 503, 3-33), WO10033617 and WO10011313, the disclosure of which is incorporated herein by reference.

In one embodiment, the crosslinks of the stapled peptide of the present disclosure are i+3, and/or i+4, and/or i+7 crosslinks. In a peptide, a "i+3 crosslink" is a crosslink between an amino acid, the "i" amino acid, and another amino acid present at a distance of 3 amino acid residues from the i amino acid. In a peptide, a "i+4 crosslink" is a crosslink between an amino acid, the "i" amino acid, and another amino acid present at a distance of 4 amino acid residues from the i amino acid. In a peptide, a "i+7 crosslink" is a crosslink between an amino acid, the "i" amino acid, and another amino acid present at a distance of 7 amino acid residues from the i amino acid.

In a particular embodiment, the peptide according to the present disclosure is a cyclic peptide. As used herein, the term "cyclic peptide" or "circular peptide" are equivalent and refers to a peptide in which the N-terminus and the C-terminus, or the N-terminus and the side chain of another amino acid, preferably the C-terminal amino acid, or the C-terminus and the side chain of another amino acid, preferably the N-terminal amino acid, or the side chain of an amino acid and the side chain of another amino acid, preferably the N-terminal amino acid and the C-terminal amino acid, are linked with a covalent bond that generates a ring structure. As used herein, the term "N-terminus", "amino-terminus", "NH2-terminus", "N-terminal end" and "amine-terminus" are equivalent and refer to the free amine group (—NH2) present on the first amino acid of the peptide. As used herein, the term "C-terminus", "carboxyl-terminus", "carboxy-terminus", "C-terminal end", and "COOH-terminus" are equivalent and refer to the free carboxyl group (—COOH) present on the last amino acid of the peptide.

The peptide may comprise a sequence according to one of the following formulae: M-(X)m-P-(X)n-R or M-(X)m-R-(X)n-P or P-(X)m-M-(X)n-R or P-(X)m-R-(X)n-M or R-(X)m-P-(X)n-M or R-(X)m-M-(X)n-P, preferably M-(X)m-R-(X)n-P or P-(X)m-R-(X)n-M or R-(X)m-M-(X)n-P or M-(X)m-P-(X)n-R, with X is any amino acid, m and n are integers from 1 to 30, and m+n is less than 50.

In these sequences, m and n are integers comprised between 1 and 30, preferably between 1 and 20, more preferably between 2 and 15, still preferably between 2 and 10, even more preferably between 2 and 7. Alternatively, m and n can be integers comprised between 3 and 5.

In these sequences, m+n is less than 50, preferably less than 30, more preferably less than 20. Alternatively, m+n can be less than 15.

In one embodiment, m and n are integers from 1 to 20 and m+n is less than 30.

In these sequences, X can be any amino acid, including M, R or P. Alternatively, X can be any amino acid except M, R and P.

In particular, X can be an amino acid favorable to an α-helix secondary structure. For instance, such an amino acid can be selected from the group consisting of A, R, D, N, C, G, Q, E, H, L, K, M, F, S, W and Y, preferably from the group consisting of A, D, N, C, G, Q, E, H, L, K, F, S, W and Y.

The peptide according to the present disclosure has a length of less than 120 amino acids. In one embodiment, the peptide according to the present disclosure has a length of less than 80 amino acids, more preferably less than 60 amino acids, still preferably less than 40 amino acids, and even more preferably less than 30 amino acids. In a particular embodiment, the peptide according to the present disclosure has a length of less than 25 amino acids. In another particular embodiment, the peptide according to the present disclosure has a length of less than 20 amino acids, preferably of less than 15 amino acids. Preferably, the peptide has a minimum length greater than 3, 4, 5, 6, 7, 8, 9, 10, 11, 12, 13, 14, 15, 16, 17, 18, 19, or 20 amino acids. For instance, the peptide has a length of at least 8 amino acids and less than 40 amino acids, preferably a length of at least 10 amino acids and less than 30 amino acids; more preferably of at least 12 amino acids and less than 25 amino acids.

In a particular embodiment, the peptide according to the present disclosure presents two, three, four or all of the following features:
- it induces insulin-independent adipocyte glucose transport;
- it comprises at least one methionine, one proline and one arginine;
- it has a length of at least 8 amino acids and less than 40 amino acids, preferably a length of at least 10 amino acids and less than 30 amino acids, more preferably of at least 12 amino acids and less than 25 amino acids;
- it adopts a secondary structure which is a helix, preferably an alpha helix;

In a more specific embodiment, the peptide according to the present disclosure presents the following features:
- it induces insulin-independent adipocyte glucose transport;
- it comprises at least one methionine, one proline and one arginine;
- it has a length of at least 8 amino acids and less than 40 amino acids, preferably a length of at least 10 amino acids and less than 30 amino acids, more preferably of at least 12 amino acids and less than 25 amino acids;
- it adopts a secondary structure which is a helix, preferably an alpha helix.
- it is stabilised by a cross-link.

In another particular embodiment, the peptide sequence according to the present disclosure comprises, consists essentially in or consists in the sequence of a segment of a PKC (Protein Kinase C). In one embodiment, the PKC is selected from conventional PKC, novel PKC and atypical PKC. In a particular embodiment, the PKC is selected from conventional PKC. Still preferably, the PKC is selected from the group consisting of α, βI, βII, and γ PKCs. Yet preferably, the PKC is selected from the group consisting of α, βI, and βII PKCs. In a more specific embodiment, the PKC is an αPKC, preferably a human αPKC, more preferably a human a PKC of SEQ ID No 1.

In one embodiment, said sequence of a segment of a PKC belongs to the sequence between positions 336 and 672 of SEQ ID No 1. For instance, the sequence of a segment of a PKC may belong to the sequences between positions 336 and 432 of SEQ ID No 1, between positions 434 and 544 of SEQ ID No 1, or between positions 568 and 596 of SEQ ID No 1.

In one embodiment, the sequence of a segment of a PKC does not include the following residues: F114, D116, C118, L121, N138, Q142, 1145, P148, G433, E545, 5562, 5566, F597, D601, W602, K604, E606, G620, T631, V664, and 1667 of SEQ ID No 1, preferably G433, E545, 5562, 5567, F597, D601, W602, K604, E606, G620, T631, V664, and 1667 of SEQ ID No 1.

Preferably, said sequence of a segment of a PKC corresponds to at least 10%, 20%, 30%, 40%, 50%, 60%, 70%, 80%, 90%, 95%, 99% of the sequence of the peptide. In a particular embodiment, the peptide sequence according to the present disclosure consist in the sequence of a segment of SEQ ID No 1.

Preferably, said at least one methionine and/or one proline and/or one arginine are included in the sequence of a segment of a PKC. More preferably, said at least one methionine and one proline and one arginine are comprised in the sequence of a segment of a PKC.

The peptide according to the present disclosure may comprise substitutions, deletions and/or additions.

Preferably, the peptide comprises no more than 20, preferably no more than 15, more preferably no more than 10, substitutions, deletions, additions, or a mixture thereof. In a particularly preferred embodiment, the peptide may comprise 1, 2, 3, 4, 5, 6, 7, 8, 9 or 10 substitution(s), deletion(s), addition(s), or a mixture thereof, preferably 1, 2, 3, 4, or 5, more preferably 1, 2 or 3. The substitution(s), deletion(s), addition(s) are not introduced at the positions of said at least one methionine, one proline, and one arginine.

In an alternative embodiment, the peptide has at least 70%, 75%, 80%, 85%, 90%, 95%, 99% of identity with the sequence of a segment of a PKC, preferably of SEQ ID No 1. In one embodiment, the part of the sequence of the peptide corresponding to SEQ ID No 1 has at least 70%, 75%, 80%, 85%, 90%, 95%, of identity with the sequence of a segment of SEQ ID No 1.

In another particular embodiment, the sequence of the peptide according to the present disclosure may comprise, consist essentially in or consist in a sequence selected from the group consisting of:

```
                                       (SEQ ID No 2)
MVEKRVLALLDKP;

(SEQ ID No 3)
PFLTQLHSCFQTVDRLYFVM;

(SEQ ID No 4)
RLYFVMEYVNGGDLMYHIQQVGKFKEP;

(SEQ ID No 5)
MYHIQQVGKFKEPQAVFYAAEISIGLFFLHKR;

(SEQ ID No 6)
PQAVFYAAEISIGLFFLHKRGIIYRDLKLDNVM;

(SEQ ID No 7)
MDGVTTRTFCGTP;

(SEQ ID No 8)
MTKHPAKR; and (SEQ ID No 12)
RKGTEELYAIKILKKDVVIQDDDVECTMVEKRVLALLDKP.

(SEQ ID No 13)
RVLALLDKPPFLTQLHSCFQTVDRLYFVM; and (SEQ ID No 14)
RTFCGTPDYIAPEIIAYQPYGKSVDWWAYGVLLYEM
``` and optionally it comprises 1, 2, 3, 4, 5, 6, 7, 8, 9, or 10 substitution(s), deletion(s), addition(s), or a mixture thereof. Preferably, it may comprise 1, 2, 3, 4, or 5 substitution(s), deletion(s), addition(s), or a mixture thereof. More preferably, it may comprise 1, 2, or 3 substitution(s), deletion(s), addition(s), or a mixture thereof. Preferably, the substitution(s), deletion(s), addition(s) are such that the at least one M, P and R are conserved. More preferably, the substitution(s), deletion(s), addition(s) are such that M, P and R are conserved. In addition, the number of substitution(s), deletion(s), addition(s) is chosen in order to keep at least 50%, 60% 70%, 75%, 80%, 85%, 90%, 95% of identity with the sequence of a segment of SEQ ID No 1.

In one aspect, the sequence of the peptide according to the present disclosure comprises, consists essentially in or consists in a sequence selected from the group consisting of:

```
                                       (SEQ ID No 2)
MVEKRVLALLDKP;

(SEQ ID No 3)
PFLTQLHSCFQTVDRLYFVM;
```

```
                                                (SEQ ID No 4)
RLYFVMEYVNGGDLMYHIQQVGKFKEP;

(SEQ ID No 5)
MYHIQQVGKFKEPQAVFYAAEISIGLFFLHKR;

(SEQ ID No 6)
PQAVFYAAEISIGLFFLHKRGIIYRDLKLDNVM;

(SEQ ID No 7)
MDGVTTRTFCGTP; and (SEQ ID No 8)
MTKHPAKR;
``` and optionally it comprises 1, 2, 3, 4, 5, 6, 7, 8, 9, or 10 substitution(s), deletion(s), addition(s), or a mixture thereof. Preferably, it may comprise 1, 2, 3, 4, or 5 substitution(s), deletion(s), addition(s), or a mixture thereof. More preferably, it may comprise 1, 2, or 3 substitution(s), deletion(s), addition(s), or a mixture thereof. Preferably, the substitution(s), deletion(s), addition(s) are such that the at least one M, P and R are conserved. More preferably, the substitution(s), deletion(s), addition(s) are such that M, P and R are conserved. In addition, the number of substitution(s), deletion(s), addition(s) is chosen in order to keep at least 50%, 60% 70%, 75%, 80%, 85%, 90%, 95% of identity with the sequence of a segment of SEQ ID No 1.

In another aspect, the sequence of the peptide according to the present disclosure comprises, consists essentially in or consists in a sequence selected from the group consisting of:

```
                                                (SEQ ID No 2)
MVEKRVLALLDKP;

(SEQ ID No 3)
PFLTQLHSCFQTVDRLYFVM;

(SEQ ID No 6)
PQAVFYAAEISIGLFFLHKRGIIYRDLKLDNVM (SEQ ID No 7)
MDGVTTRTFCGTP;

(SEQ ID No 8)
MTKHPAKR;
``` and optionally it comprises 1, 2, 3, 4, 5, 6, 7, 8, 9, or 10 substitution(s), deletion(s), addition(s), or a mixture thereof. Preferably, it may comprise 1, 2, 3, 4, or 5 substitution(s), deletion(s), addition(s), or a mixture thereof. More preferably, it may comprise 1, 2, or 3 substitution(s), deletion(s), addition(s), or a mixture thereof. Preferably, the substitution(s), deletion(s), addition(s) are such that the at least one M, P and R are conserved. More preferably, the substitution(s), deletion(s), addition(s) are such that M, P and R are conserved. In addition, the number of substitution(s), deletion(s), addition(s) is chosen in order to keep at least 50%, 60% 70%, 75%, 80%, 85%, 90%, 95% of identity with the sequence of a segment of SEQ ID No 1.

In a particular aspect, the sequence of the peptide according to the present disclosure comprises, consists essentially in or consists in a sequence selected from the group consisting of:

```
                                                (SEQ ID No 2)
MVEKRVLALLDKP;

(SEQ ID No 7)
MDGVTTRTFCGTP;

(SEQ ID No 8)
MTKHPAKR;
``` and optionally it comprises 1, 2, 3, 4, 5, 6, 7, 8, 9, or 10 substitution(s), deletion(s), addition(s), or a mixture thereof. Preferably, it may comprise 1, 2, 3, 4, or 5 substitution(s), deletion(s), addition(s), or a mixture thereof. More preferably, it may comprise 1, 2, or 3 substitution(s), deletion(s), addition(s), or a mixture thereof. Preferably, the substitution(s), deletion(s), addition(s) are such that the at least one M, P and R are conserved. More preferably, the substitution(s), deletion(s), addition(s) are such that M, P and R are conserved. In addition, the number of substitution(s), deletion(s), addition(s) is chosen in order to keep at least 50%, 60% 70%, 75%, 80%, 85%, 90%, 95% of identity with the sequence of a segment of SEQ ID No 1.

Alternatively, the sequence of the peptide according to the present disclosure comprises, consists essentially in or consists in a sequence selected from the group consisting of:

```
                                                (SEQ ID No 9)
VECTMVEKRVLALLDKPPFLTQLHS;

(SEQ ID No 10)
MCKEHMMDGVTTRTFCGTPD; and (SEQ ID No 11)
SICKGLMTKHPAKRLGCGPEG;
``` and optionally it comprises 1, 2, 3, 4, 5, 6, 7, 8, 9, 10, 11, 12, 13, 14, or 15 substitution(s), deletion(s), addition(s), or a mixture thereof. Preferably, it may comprise 1, 2, 3, 4, 5, 6, 7, 8, 9, or 10 substitution(s), deletion(s), addition(s), or a mixture thereof. More preferably, it may comprise 1, 2, 3, 4, or 5 substitution(s), deletion(s), addition(s), or a mixture thereof. Preferably, the substitution(s), deletion(s), addition(s) are such that the at least one M, P and R are conserved. More preferably, the substitution(s), deletion(s), addition(s) are such that M, P and R are conserved. In addition, the number of substitution(s), deletion(s), addition(s) is chosen in order to keep at least 50%, 60% 70%, 75%, 80%, 85%, 90%, 95% of identity with the sequence of a segment of SEQ ID No 1.

In a particular aspect, the peptide comprises, consists essentially in or consists in a sequence selected from the group consisting of:

```
                                                (SEQ ID No 9)
VECTMVEKRVLALLDKPPFLTQLHS;

(SEQ ID No 10)
MCKEHMMDGVTTRTFCGTPD; and (SEQ ID No 11)
SICKGLMTKHPAKRLGCGPEG;
``` wherein the residues which are bold and underlined carry the stapling.

Optionally the peptide according to the present disclosure further comprises 1, 2, 3, 4, 5, 6, 7, 8, 9 or 10 substitution(s), deletion(s), addition(s), or a mixture thereof in the above listed sequences. Preferably, it may comprise 1, 2, 3, 4, 5, 6, 7, 8, 9, or 10 substitution(s), deletion(s), addition(s), or a mixture thereof. More preferably, it may comprise 1, 2, 3, 4, or 5 substitution(s), deletion(s), addition(s), or a mixture thereof. The substitution(s), deletion(s), addition(s) is chosen in order to conserve the at least one M, P and R and the two residues used for the stapling. More preferably, the substitution(s), deletion(s), addition(s) are such that M, P and R are conserved.

The peptide according to the present disclosure may further comprise a moiety facilitating its cellular uptake or entry, in particular a PTD (protein transduction domain). PTD generally comprises a certain amino acid sequence of 10 to 20 amino acids (Matsushita and Matsui, (2005), J Mol Med 83, 324-328; Vivès et al, Biochimic et Biophysica Acta, 2008, 1786, 126-138). PTD is mainly composed of basic amino acids such as arginine or lysine, and representative examples of the PTD include arginine rich peptides such as poly $R_8$ (RRRRRRRR (SEQ ID No 15)) or (RRPRRPRR-PRRPRRP (SEQ ID No 16)), antennapedia or penetratin peptide such as (RQIKIWFQNRRMKWKK (SEQ ID No 17)) or HIV-Tat (YGRKKRRQRRR (SEQ ID No 18)).

The peptide according to the present disclosure can be made of natural amino acids and/or unnatural amino acids, preferably at least one methionine, one proline, and one arginine are natural amino acids. The term "unnatural amino acids" is defined as an analog or derivative of a natural amino acid (i.e., Alanine, Valine, Glycine, Leucine, Isoleucine, Lysine, Arginine, Glutamic acid, Glutamine, Aspartic acid, Asparagine, Histidine, Tyrosine, Phenylalanine, Tryptophan, Serine, Proline, Threonine, Cysteine, Methionine). They present a modified side chain, e.g. shorter, longer or with different functional groups. Isomers D and L are contemplated, in particular because isomers D are not sensible to proteases. In addition, modifications in some or all peptide bounds are also contemplated in order to increase the proteolysis resistance, in particular by (—CO—NH—) by (—CH$_2$—NH—), (—NH—CO—), (—CH$_2$—O—), (—CH$_2$—S—), (—CH$_2$—CH$_2$—), (—CO—CH$_2$—), (—CHOH—CH$_2$—), (—N=N—), and/or (—CH=CH—). The peptide can present a carboxylic C terminal end (—COO$^-$) and an amide one (—CONH$_2$). The peptide can also be D-retro-inverso sequence of a peptide as disclosed herein. The N terminal can be modified, especially with an acetyl radical.

Optionally, the peptide can be PEGylated in order to increase its stability. Further optionally the peptide can be formulated in non-aqueous protic solvent solutions such as propylene glycol and polyethylene glycol. The peptide may also be packaged into poly lactic co-glycolic acid microsphere depot formulation. Many sustained-release delivery systems exist, and many of these are appropriate for use in the present disclosure. For example, polymer-based slow-release compositions based upon degradable polymers such as PLGA, poly-lactate or poly-glycolate are suitable, as are lipid-based depot compositions, such as those described in WO2005/117830 and/or WO2006/075124, the complete disclosures of which are being hereby incorporated by reference. The formulation of active agents into biodegradable polymer depot formulations is well established and well known in the art, and the peptides of the present disclosure may thus be formulated with these using known methods. Preferably, the composition of the present disclosure is capable of releasing the peptide at a functional concentration for at least 1 month.

In an additional aspect, the peptide according to the present disclosure induces insulin-independent adipocyte glucose uptake. The insulin-independent adipocyte glucose uptake can be assessed by any method known from the man skilled in the art. In particular, it is assessed by the method described in the example section. Peptides that induce insulin-independent adipocyte glucose uptake can be conveniently screened for using any technology known in the art, in particular any method suitable for measuring transport of glucose into adipocytes in cell culture. A particular technique for assessing the effect of the peptide is to measure either fluorescently or radioactively or colorimetrically the amount of glucose or glucose analogue inside the adipocyte. The inventors have found a preferable method to induce adipocyte insulin-independent glucose uptake is to use peptides or compounds that bind ALMS1 and thereby block the interaction in adipocytes between endogenous αPKC and ALMS1. Accordingly, in one embodiment, the peptide is capable of preventing or releasing the binding of αPKC to ALMS1. This then trigger adipocyte insulin-independent glucose uptake. To determine the ability of a peptide or compound to block binding of αPKC to ALMS1 any technology known by the person skilled in the art can be carried out, in particular any method suitable for determining protein interactions. For example, recombinant or purified native ALMS1 or αPKC can be bound to a surface plasmon resonance ship and the other molecule flowed over the chip to assess the binding affinity, for example in a Biacore (General Electric, USA) machine. The same approach can be used to measure the binding affinity of ALMS1 and αPKC.

The effect of the peptide on the binding of αPKC to ALMS1 is determining by measuring the binding of αPKC to ALMS1 in absence and in presence of the tested molecule and by comparing the bindings of αPKC to ALMS1. Due to the large size of ALMS1, the inventors prefer using cellular systems for the screening methods. Preferably, the cellular system is a cellular system responsive to insulin. For instance, the cellular system could be selected among a mesenchymal cell line, a mesenchymal stem cell, an adipose mesenchymal stem cell, a pre-adipocyte and an adipocyte. Preferably, the cell is a human cell. Then, the binding determinations can be carried in absence or presence of insulin, preferably in the absence of insulin for the binding of αPKC to ALMS1.

In a first aspect, immunoprecipitation assay using ALMS1 as bait can be undertaken, in particular as detailed in the experimental section. For instance, the assay can be carried out with cells, in particular adipocytes, cultured in absence and/or presence of insulin, preferably in absence of insulin. The peptides to be tested are added in the culture medium. Then, αPKC is immunodetected.

In one embodiment, the amount of αPKC bound to ALMS1 is determined and compared to the amount in absence of tested peptides, in particular in absence of insulin. If the amount of αPKC bound to ALMS1 decreases in presence of the tested peptide, then the peptide is selected. In a second aspect, affinity purification coupled to mass spectrometry can be carried out, in particular after chemical crosslinking. For instance, cells may be cultured in a medium devoid of methionine and leucine but comprising photo-activable methionine and leucine. Then, cells are UV irradiated in order to stabilize protein complexes and protein complexes are analyzed by mass spectrometry.

By "increased", "increase" or "enhance" is intended to refer to a binding increased by at least 10, 20, 30, 40, 50, 60, 70, 80 or 90% when compared to the binding measured in absence of the tested molecule in the same conditions. By "decreased" or "decrease" is intended to refer to a binding decreased by at least 10, 20, 30, 40, 50, 60, 70, 80 or 90% when compared to the binding measured in absence of the tested molecule in the same conditions.

Therapeutic Indications

The present invention further relates to a pharmaceutical composition comprising a peptide as defined above and a pharmaceutically acceptable carrier/excipient and optionally another active ingredient. It also relates to a peptide as defined above for use as a drug or to the use of a peptide as defined above for the manufacture of a medicament.

Diabetes mellitus is characterized by hyperglycemia. More particularly, type 2 diabetes is characterized by hyperglycemia and insulin resistance. Obesity is thought to be the primary cause of type 2 diabetes in people who are genetically predisposed to that disease. Diabetic retinopathy, diabetic neuropathy, diabetic nephropathy are well-known disorders associated with diabetes and insulin resistance.

A finding of the present invention is that peptides of the present disclosure inducing adipocyte glucose uptake are surprisingly effective at reversing hyperglycaemia caused by obesity. The inventors propose to use the peptides and pharmaceutical compositions as disclosed herein for inducing glucose uptake, in particular by adipocytes, thereby resulting in improved blood glucose control. Then, the peptides and pharmaceutical compositions are suitable for treating or delaying the progression or onset of diabetes mellitus, insulin resistance, hyperlipidaemia, coronary heart disease, diabetic retinopathy, diabetic neuropathy, diabetic nephropathy, insulin resistance, hyperglycemia, obesity, lipodystrophy, insulin deficiency, beta cell dysfunction or hyperinsulinaemia.

The present invention relates to a method for the treatment or prevention of hyperglycaemia, in particular through induction of insulin-independent adipocyte glucose uptake, comprising administering a peptide according to the present disclosure or a pharmaceutical composition comprising it. Induction of insulin-independent adipocyte glucose uptake is shown to be able to restore normoglycaemia and correct downstream metabolic defects in diabetic individuals. It also relates to the use of a peptide according to the present disclosure or a pharmaceutical composition comprising it for the manufacture of a medicine for the treatment or prevention of hyperglycaemia, in particular through induction of insulin-independent adipocyte glucose uptake. In addition, it relates to a peptide according to the present disclosure or a pharmaceutical composition comprising it for use for the treatment or prevention of hyperglycaemia, in particular through induction of insulin-independent adipocyte glucose uptake.

The present invention also relates to the peptides and pharmaceutical compositions according to the present disclosure for use for reducing the dose of insulin or stopping the insulin treatment when used for treating diabetes in a subject, to the use of the peptides according to the present disclosure for the manufacture of a medicament for reducing the dose of insulin or stopping the insulin treatment when used for treating diabetes in a subject, or to a method for treating diabetes in a subject, wherein a therapeutically effective amount of a peptide or a pharmaceutical composition according to the present disclosure is administered to a subject with a decreased dose of insulin or in absence of insulin treatment. More generally, the peptide or pharmaceutical composition according to the present disclosure can be used to lower the doses of anti-diabetic drugs. The present invention relates to the pharmaceutical or veterinary use of the peptide. Accordingly, the subject may be any mammal, preferably a human subject, including adult, child, newborn or human at the prenatal stage. In a particular embodiment, the subject is a subject suffering from obesity. Optionally, the subject has no detectable anti-islet antibodies, and no pancreatic abnormalities. In the context of a veterinary application, the subject can be an animal, preferably a mammal, in particular a pet animal such as a dog, a cat, a horse, a donkey, a rabbit, a ferret, a gerbil, a hamster, a chinchilla, a rat, a mouse, or a guinea pig.

The peptide(s) according to the present disclosure can be used in combination with one or more additional active drugs, preferably anti-diabetic or anti-obesity drugs, in particular for treating or delaying the progression or onset of diabetes mellitus, insulin resistance, hyperlipidaemia, coronary heart disease, diabetic retinopathy, diabetic neuropathy, diabetic nephropathy, insulin resistance, hyperglycemia, obesity, lipodystrophy, insulin deficiency, beta cell dysfunction or hyperinsulinaemia.

Therefore, the present invention also relates to a pharmaceutical composition comprising peptide(s) according to the present disclosure and one or more additional active drugs, preferably an anti-diabetic drug.

It further relates to a product or kit containing a pharmaceutical composition according to the present disclosure and one or more additional active drugs, preferably anti-diabetic drugs, as a combined preparation for simultaneous, separate or sequential use, or a combined preparation which comprises a peptide according to the present disclosure and one or more additional active drugs, preferably anti-diabetic drugs, for simultaneous, separate or sequential use, in particular for treating or delaying the progression or onset of diabetes mellitus, insulin resistance, diabetic retinopathy, diabetic neuropathy, diabetic nephropathy, insulin resistance, hyperlipidaemia, coronary heart disease, hyperglycemia, obesity, lipodystrophy, insulin deficiency, beta cell dysfunction or hyperinsulinaemia.

It yet further relates to a pharmaceutical composition according to the present disclosure for use for treating or delaying the progression or onset of diabetes mellitus, insulin resistance, hyperlipidaemia, coronary heart disease, diabetic retinopathy, diabetic neuropathy, diabetic nephropathy, insulin resistance, hyperglycemia, obesity, and hyperinsulinaemia in combination with one or more additional active drugs, preferably anti-diabetic drugs.

It still further relates to a pharmaceutical composition according to the present disclosure and one or more additional active drugs, preferably anti-diabetic drugs, for the manufacture of a medicament, in particular for treating or delaying the progression or onset of diabetes mellitus, insulin resistance, hyperlipidaemia, coronary heart disease, diabetic retinopathy, diabetic neuropathy, diabetic nephropathy, insulin resistance, hyperglycemia, obesity, and hyperinsulinaemia.

Finally, it relates to a method for treating or delaying the progression or onset of diabetes mellitus, insulin resistance, hyperlipidaemia, coronary heart disease, diabetic retinopathy, diabetic neuropathy, diabetic nephropathy, insulin resistance, hyperglycemia, obesity, and hyperinsulinaemia, wherein a therapeutic effective amount of a pharmaceutical composition according to the present disclosure is administered in combination with a therapeutic or sub-therapeutic effective amount of one or more additional active drugs, preferably anti-diabetic drugs. By "sub-therapeutic" is intended to refer to an amount that can be for instance 90, 80, 70, 60, 50, 40, 30, 20 or 10% of the conventional therapeutic dosage (in particular for the same indication and the same administration route).

In particular, the additional active drug is a drug used for treating or delaying the progression or onset of diabetes mellitus, insulin resistance, hyperlipidaemia, coronary heart disease, diabetic retinopathy, diabetic neuropathy, diabetic nephropathy, insulin resistance, hyperglycemia, obesity, and hyperinsulinaemia. For instance, the additional drug can be an anti-diabetic drug such as a hypoglycemic agent or an antihyperglycemic agent. It may be selected in the non-exhaustive list comprising insulin, metformin, sulfonylureas such as tolbutamide, acetohexamide, tolazamide, chlorpropamide, glyburide, glimepiride, glipizide, glicazide, glycopyramide and gliquidone, alpha-glucosidase inhibitors such as acarbose, miglitol and voglibose, thiazolidinediones such as pioglitazone and rosiglitazone, a meglitinide such as repaglinide and nateglinide, incretin mimetics, glucagon-like peptide analogs and agonists such as exenotide, taspoglutide and liraglutide, dipeptidyl peptidase-4 inhibitors such as vildagliptin, sitagliptin, saxagliptin, linagliptin, alogliptin, and septagliptin, amylin analogs such as pamlintide, glycourics such as canagliflozin, emplagliflozin and dapagliflozin, or any combination thereof.

The form of the pharmaceutical compositions, the route of administration, the dosage and the regimen naturally depend upon the condition to be treated, the severity of the illness, the age, weight, and sex of the patient, etc.

The pharmaceutical or therapeutic compositions of the present disclosure can be formulated for a topical, oral, parenteral, intranasal, intravenous, intramuscular, subcutaneous or intraocular administration and the like.

The peptide used in the pharmaceutical composition of the present disclosure is present in a therapeutically effective amount.

The pharmaceutical composition comprising the peptide is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

In one aspect, the present invention provides a stable formulation for parenteral injection of the pharmaceutical composition according to the present disclosure comprising a peptide or a salt thereof, wherein the peptide has been dried and then is reconstituted in a solvent prior to use. The peptide (or, in embodiments where the formulation comprises two or more peptides, each of the peptides) is mixed with a non-volatile buffer and dried to a dry peptide powder. Suitable buffers include, but are not limited to, glycine buffers, citrate buffers, phosphate buffers, and mixtures thereof. In one embodiment, the buffer is a glycine buffer. In another embodiment, the buffer is a mixture of citrate buffer and phosphate buffer. In some embodiments, wherein the formulation comprises two or more peptides, the first and second buffer are the same. In some embodiments, wherein the formulation comprises two or more peptides, the first and the second buffer are different. Alternatively, the pharmaceutical composition according to the present disclosure may be stored in an aqueous state. The solution may contain, if desired, further additives or excipients, which must be compatible with the active principle and, if they are not removed during the freeze-drying stage, they must also be compatible with the route of administration. For parenteral administration the composition may be injected intradermally, subcutaneously, intramuscularly, or intravenously. It may preferably be placed with a mini-osmotic pump or other controlled delivery device implanted into the body. Preferably, it may be mixed with other compounds to make a depot slow release formulation. A preferred route of administration is subcutaneous injection using a disposable or multiunit dispensing device, similar to an insulin pen.

In one embodiment, the peptide of the present disclosure may be mixed with other compounds to make a depot slow release formulation. This may then be injected subcutaneously to form a slow release depot.

For oral administration, the composition can be formulated into conventional oral dosage forms such as tablets, capsules, powders, granules and liquid preparations such as syrups, elixirs, and concentrated drops. Non-toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, intrapulmonary inhalation, rectal or vaginal suppositories can be used. In one embodiment, the invention may be administered by the intrapulmonary route using either a dry powder or liquid formulation administered using an intrapulmonary drug delivery device according to methods known in the art. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the present disclosure may be formulated to release the active drug substantially immediately upon administration or at any predetermined time or time period after administration.

Pharmaceutical compositions according to the present disclosure can comprise one or more peptides of the present disclosure associated with pharmaceutically acceptable excipients and/or carriers. These excipients and/or carriers are chosen according to the form of administration as described above.

In a particular embodiment, the pharmaceutical composition according to the present disclosure comprises between 10 ng and 10 g of the peptide of the present disclosure. In one embodiment, pharmaceutical composition according to the present disclosure comprises between 0.01 mg and 1 g of the peptide of the present disclosure.

All the references cited in this application, including scientific articles and summaries, published patent applications, granted patents or any other reference, are entirely incorporated herein by reference, which includes all the results, tables, figures and texts of theses references.

Although having different meanings, the terms "comprising", "having", "consisting in" and "containing" can be replaced one for the other in the entire application.

Further aspects and advantages of the present disclosure will be described in the following examples, which should be regarded as illustrative and not limiting.

EXAMPLES

Material and Method

Animal Husbandry

Animal studies were performed in accordance with the recommendations of the local ethical comity. Alms1$^{foz/foz}$ (fat Aussie; FA) mice and Alms1$^{+/+}$ (WT) littermates were maintained on a C57BL/6J background under pathogen free conditions in a 12 hourly light/dark cycle. Mice had free access ad libitum to water and normal chow diet. Primers flanking the foz mutation were used for PCR genotyping: forward ACA ACT TTT CAT GGC TCC AGT (SEQ ID No 19); reverse TTG GCT CAG AGA CAG TTG AAA (SEQ ID No 20). For the diet induced obese and glucose intolerant mice, C57/Black 6 male mice had free access ad libitum to water and 60% high fat/high glucose diet.

Insulin Tolerance Test (ITT) and Glucose Tolerance Test (GTT)

Mice were tested for insulin resistance by ITT and intraperitoneal GTT. The ITT was performed on 4 h fasted mice. Insulin (Humulin R, Eli Lilly, USA) was injected i.p. at 0.5 U/kg body weight in 0.9% saline (Pfizer, USA). The GTT was performed on 18 h fasted mice. Glucose was injected with 2 g/kg bodyweight in 0.9% saline. The tail was snipped for blood collection and the plasma glucose was determined at 0, 15, 30, 60 and 120 min in the GTT using a glucometer (Optium Xceed, Abbott, USA). Alternatively, plasma insulin measurement was performed using blood from 4h fasted mice collected on conscious animals via submandibular bleeding and analyzed for fasting insulin using a commercial ultrasensitive mouse insulin ELISA kit (Crystal Chem Inc., USA).

AdipoRed Staining of Adipose Tissue

Fat tissue of 60 d and 120 d old mice were isolated and briefly washed in PBS (3.2 mM Na2HPO4, 0.5 mM KH2PO4, 1.3 mM KCl, 135 mM NaCl, pH 7.4). Samples were then placed in 4% paraformaldehyde (in 0.1M sodium phosphate buffer, pH 7.2) for 15 min, washed in PBS and incubated in AdipoRed dye (1/25; Lonza, Switzerland) with 30 µM DAPI (Sigma-Aldrich, USA) for 15 minutes. After 3 washes with PBS samples were mounted on slides and pictures were taken using BX50 fluorescence microscope (Olympus, Japan).

Insulin-Dependent Glucose Uptake

High fat-fed (Specialty feed; SF03-020; 23% fat, 0.19% cholesterol, simple carbohydrates, based on AIN93G) mice were fasted for 3-6 hours before start of experiment. Insulin 0.75 U/kg was injected i.v. via the tail vein in combination with 3 µCi of 2-[1-C$^{14}$] deoxy-D-glucose (DOG) (Perkin Elmer, Australia). Blood glucose and samples were collected at 0, 5, 10, 15, 20, 40, and 60 min after injection from the tail. Mice were sacrificed (cervical dislocation) and liver, muscle (both sides soleus, and EDL=glycolytic muscles; left thigh), heart, subcutaneous adipose tissue, visceral adipose tissue (peri-renal) were isolated and rinsed in ice-cold PBS, quickly dried on flint-free paper tissue and weighed. Then, a piece of the isolated tissue was chopped into small pieces, weighed again then homogenized for 1 h at 60° C. in 1N NaOH then neutralized with HCl (1M). One part of the homogenate was used to determine deoxyglucose+deoxyglucose-6-P by precipitating proteins with 6% perchloro acid (PCA) and the supernatant measured by scintillation counter (Perkin Elmer). The other part was mixed with 0.3N ZnSO$_4$ to react with deoxy-glucose-6-P and the complex was precipitated with 0.3N Ba(OH)$_2$ and the supernatant used for scintillation measurement.

Alms1$^{ftin/ftin}$; Adiponectin-Cre$^{+/-}$ Glucose Phenotyping

So far, our approach has been based on targeting the adipose tissue glucose reabsorption as it has been fueled by our previous finding that only the adipose tissue in the ALMS mutant mouse was not absorbing infused radioactive glucose. In order to fully demonstrate that it is the adipose tissue and only the adipose tissue, that is driving the diabetic phenotypic in the ALMS mice, we intend to specifically inactivate the ALMS1 gene in the adipose tissue and subsequently perform a glucose tolerance test (GTT). In this way, we will prove that the adipose tissue, although absorbing only 20% of the circulating glucose, is a major player in controlling systemic glycaemia thereby establishing that our peptide approach targeting the adipose tissue to restore glucose homeostasis is a pertinent one.

ALMS1 Modelling

The ALMS1 3D model was constructed using a fragment modeling method with the homology modelling program Modeler. The amino acid sequence for each exon of Alms1 was submitted to profile based threading algorithm available at PISRED server and suitable templates were identified. Then those identified template proteins were aligned with the respective exon sequences and each exon was modelled separately using Modeller. The energy optimization and selection of models were conducted based on discrete optimized protein energy score. Finally, models were assembled to construct the structure of full length Alms1 and the full length protein was relaxed and minimized using the molecular dynamics simulation program NAMD.

In Vitro Characterization of the Effect of the Peptide Expression in the Adipocyte Human white visceral preadipocytes (Catalog #: C-12732; PromoCell) were purchased. The preadipocytes were seeded according to manufacturer's protocol and cultured in the Preadipocyte growth medium (Catalog #: C-27410; Promo-Cell) to confluence. Once confluence was reached, adipogenic differentiation was triggered through medium change to get mature human adipocytes. For the culture without insulin, Adipocyte Basal Medium (Catalog #: C-2431; PromoCell) without insulin was complemented with 5 g/L of deoxyglucose, 8 µg/mL d-Biotin, 400 ng/mL Dexamethasone (following manufacturer's procedure). Native peptides and their stapled counterparts as well as the scrambled peptides (corresponding to the same set of amino acids but rearranged randomly) were purchased from Eurogentec. Each peptide was diluted in saline and used at a dose of 2.5 ng per 10 cm square of cell culture surface area for in vitro studies or 2.5 ng of each peptide (A and B) was injected per mouse.

Fluorescence Imaging Experiments

The cells were seeded on permanox 8-wells Lab-Tek II Chamber Slide (Catalog #: 177445; NUNC). Cells were treated as indicated. Then both cells and tissues cryosections were processed for protein detection after methanol fixation and permeabilized with 0.1% Triton X-100. The microscopy slides were mounted for detection with Vectashield Mounting Medium (Catalog #: H-1200; Vector Laboratories). To view membrane-associated proteins, cells were formalin fixated for 15 min and were directly blocked, followed by immunostaining and acquisition using an upright Zeiss Axiolmager Z2 microscope. Image analysis, 3D reconstitution and Time Lapse experiments and endosomes tracking experiments were performed using either the Zeiss AxioVision program with the corresponding 3D and Tracking Zeiss modules or the Zeiss Zen 2012 imaging platform. For in vitro glucose absorption, the cells were incubated for 30 minutes with the fluorescent glucose analogue 2-NBDG together with DAPI for the nuclear counterstaining. The cells were then washed with normal culture medium and pictures were acquired.

In Vitro Assessment of Glucose Absorption for the Selected Peptides

Mature adipocytes were cultured in 96 well plate. The adipocytes received the different peptides at the indicated concentration above. 24 hours later, the glucose absorption capacity if the treated cells were assessed using the Glucose Uptake Colorimetric Assay kit from Bio Vision (Catalog #: K676-100).

Acute Tolerance Test for the Two Peptides in Different Mouse Models (Diet Induced Diabetic WT, Control Non Obese Chow-Fed, FA Mouse) Protocol Working stock of each tested peptide 10 ng/mL in saline solution
Make a solution of Glucose 22% (1:2 Glucose; NaCl).or NaCl 0.9%
Fast mice for 4-5 hours prior to peptide injection.
Weigh each mouse and calculate the average and multiply by the number of mice (count 2 mice more).
For the peptides injection 2.5 µL peptide A and 2.5 µL peptide B per mouse. Multiply 2.5 µL peptide A and B per number of mice.
Average of mice×(number of mice+2)=X1
X1×10=total volume (TV)
Volume of Glucose 22%=TV−(2.5 peptide A×(number of mice+2))+(2.5 peptide B×(number of mice+2))
Prepare the volume of each syringe for each mouse 100 µL/10 g.
Cut 1 mm of tail and measure the glycaemia with glucometer "Startrip" (T0).
Inject the glucose to each animal, injection must be intraperitoneal at the right side, insert the needle about 1 cm.
Take measures with the glucometer every 30 minutes until 120 minutes.
Following the GTT to monitor the anti-diabetic effect of the peptides, we euthanized the mice and sampled the different tissues. After formalin fixation, the fixated adipose tissue was incubated with AdipoRed and DAPI for 30 minutes. After 2 washes with PBS buffer, the adipose tissue was mounted on glass slides for image acquisition. For the other tissues, cryosections were performed and were stained in a similar way as the adipose tissue.

Example 1: Alms1$^{foz/foz}$ Mice Glucose Phenotyping

Alström syndrome mouse model the Alms1$^{foz/foz}$ is, at six-month of age, obese (FIG. 1A) and presents hypertrophy of the adipose tissue (FIG. 1B) together with severe insulin resistance (FIG. 1C). When tested at 2 month of age, where neither the obese phenotype nor the adipose tissue hypertrophy has developed, the Alms1$^{foz/foz}$ nevertheless exhibited severe insulin resistance (FIG. 1F) indicating that the diabetic phenotype is not secondary to the obese phenotype. Insulin-stimulated deoxyglucose uptake studies showed impaired uptake restricted to WAT in Alms1$^{foz/foz}$ with compensatory increased deoxyglucose uptake by muscle (FIG. 1H), pointing to a specific defect in adipocyte glucose transport as the primary site of insulin resistance in Alms1$^{foz/foz}$ mice.

Example 2: Alms1$^{ftin/ftin}$ Adiponectin Cre Glucose Phenotyping

Figure 2:
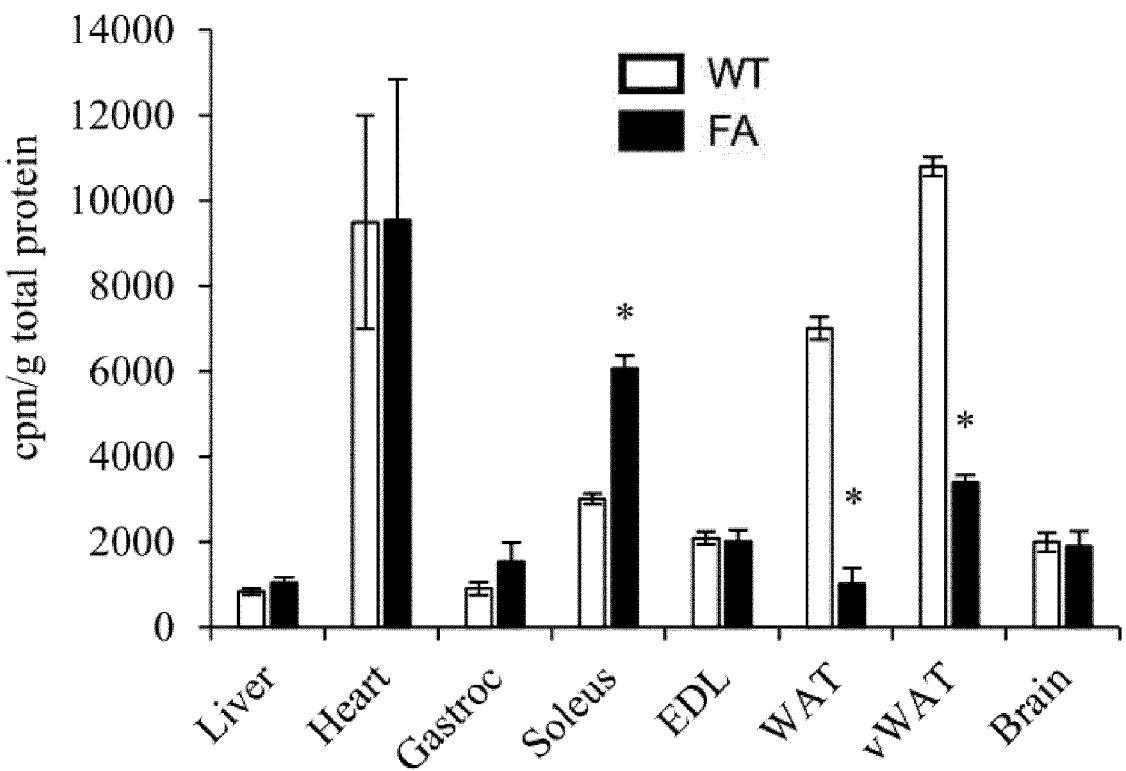
FIG. 2: Generation of a specific adipose tissue re-activation of ALMS1 (Alms$^{ftin/ftin}$) and its metabolic characterization
(A) Schematic representation representing the cloning strategy for generating the specific reintroduction of ALMS activity in the targeted tissue through Cre activity with the stop sequence of the neomycin gene (NEO box) was introduced in the intronic region of the ALMS gene and was then flanked with 2 LoxP sites.
(B) Upon Cre activity, the floxed region is removed leaving only one LoxP site with no stop codon reactivating the ALMS 1 expression.
(C) Specificity assessment of the Adiponectin-Cre mouse line for the adipocyte only. By crossing Adiponectin-Cre with the RosaTomatoeGFP reporter line, only the tissue which turns fluorescent indicates Cre activity.
(D) Quantitative PCR analysis of the Alms1 expression levels in the different target tissue with the given genotype. In the WT mouse, all the tested tissues are expressing ALMS1 and in the Alms1$^{ftin/ftin}$ no expression level is detected, whereas in the Alms1$^{ftin/ftin}$; Adiponectin-Cre$^{+/-}$, only the adipose tissue is expressing ALMS1.
Figure 2:
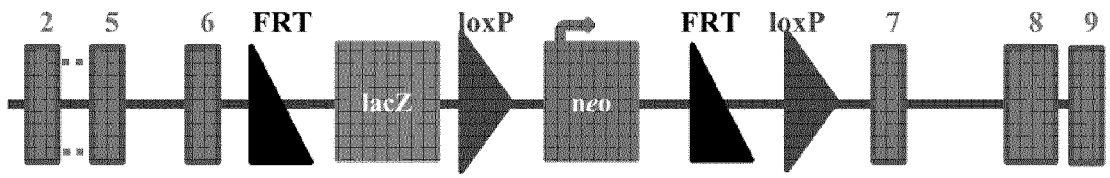
Figure 2:
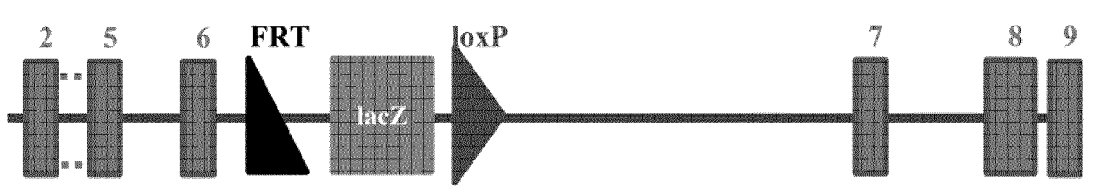

Next, the inventors generated a mouse line where the Alms1 allele was targeted with a construct that would specifically introduce a lacZ and a Neomycin coding sequence flanked with either the Frt or the LoxP site as indicated (FIG. 2A). The introduction of this sequence in the ALMS allele prevents its proper expression and hence results in a knockout mouse model for the ALMS gene (Alms1$^{ftin/ftin}$). On the other hand, by using the Cre-LoxP technology, the Neomycin coding sequence can be removed (FIG. 2B) and hence restore the expression of the complete ALMS gene. Concerning the validation of the specificity of the Adipo-Cre mouse to solely target the adipocytes, the inventors used a reporter mouse line RosaTomatoeGFP in which tissue turns green upon Cre activity, the results show specific Cre activity in the adipocytes which corresponded in the specific re-activation of ALMS1 expression in the adipose tissue (FIG. 2C). Quantitative PCR for the normalized expression level of Alms1 in different target tissues revealed complete inactivation of ALMS1 in the different tissues except in the adipose tissue of the Alms1$^{ftin/ftin}$; Adiponectin-Cre$^{+/-}$mice (FIG. 2D). Metabolic phenotyping of the Alms1$^{ftin/ftin}$ mice for body weight over time and GTT were performed at 2 months. Alms1$^{ftin/ftin}$ mice became obese and glucose intolerant (FIG. 2E-F). Alms1$^{ftin/ftin}$; Adiponectin-Cre$^{+/-}$mice which have a specific restoration of ALMS1 in the adipose tissue were protected against obesity and glucose intolerance showing that ALMS1 role in the adipose tissue is crucial for glucose homeostasis.

Example 3: In Silico Prediction of αPKC Binding on ALMS

Based on the in silico modelling of αPKC with ALMS1, we identified 3 key amino acid residues, namely Methionine, arginine and proline. By searching in the complete αPKC protein sequence for these 3 amino acid residues, 3 potential peptide sequences were shortlisted (peptides of SEQ ID No 9, SEQ ID No 11, and SEQ ID No 10, called Peptide A, peptide B and peptide C respectively).

Example 4: In Vitro Characterization of the Effect of the Peptide on Glucose Absorption in the Human Adipocyte Native peptides were stabilized using the stapling technology and labelled at the N-terminal with FAM (green). Cell penetrance of peptide A and B on human adipocytes was assessed by imaging with the membrane stained in red and the nuclei in blue. (FIG. 4A). Two FAM-labelled different peptides A and B were tested for cellular entry and 3D images of adipocytes showing intracellular localization of the peptides (FIG. 4B).

In FIG. 4C, the fluorescent images show the peptides A and B mediate cellular entry of the fluorescent glucose analogue in the adipocytes in the absence of Insulin.

FIG. 4D-E depicts the efficacy assessment of the peptides A and B either in their native form or in the stapled form to trigger glucose entry in the adipocytes. Both peptides A and B under native condition are able to trigger a significant entry of glucose into the adipocyte in absence of insulin. Stapled peptides which are resistant to degradation and therefore more stable have a higher activity in absence of insulin.

Example 5: Testing the Peptides In Vivo for Anti-Diabetic Properties

Figure 1:
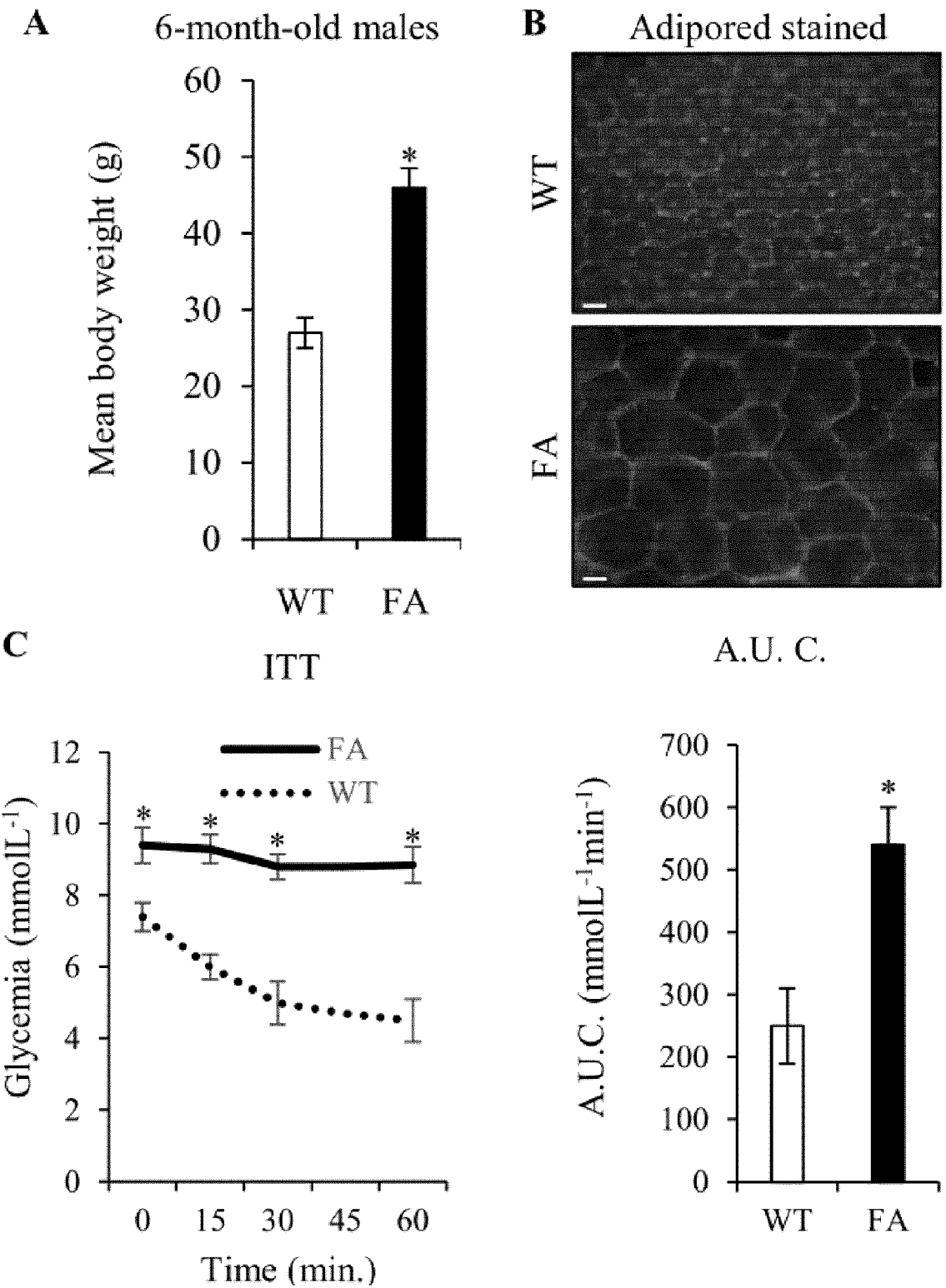
FIG. 1. Metabolic characterization of FA mice
(A) Mean body weight from 6-month-old male mice.
(B) Visceral adipose tissue from 6-month-old male mice stained with Adipo-red. Scale bar: 25 μM
(C) Insulin tolerance test (ITT) and corresponding histogram showing area under the curve (A.U.C.) p<0.001) from 6-month-old male mice.
(D) Mean body weight from 2-month-old male mice.
(E) Visceral adipose tissue from 2-month-old male mice stained with Adipo-red. Scale bar: 25 μM
(F) ITT and histogram showing A.U.C. from 2-month-old male mice
(G) Measurement of insulin-stimulated deoxyglucose uptake levels in 2-month-old mice in different organs: liver, heart, gastrocnemius muscle, soleus, EDL (extensor digitorum longus muscle), WAT (white adipose tissue), vWAT (visceral WAT), brain. (n=6-8 mice per genotype).

In vivo assessment of the effect of stapled peptides A and B injection in the adipose tissue of diet-induced diabetic WT mice. Mice were fed with a defined high fat/high glucose diet until they became intolerant to glucose (FIG. 5A, Prior Injection). Once the mice were glucose intolerant, these mice received an injection with a combination of the stapled peptides A and B directly in the subcutaneous fat and GTT was again performed a week later as depicted in FIG. 5B. Following the peptide injection, GTT on the mice, showed significant improvement of glucose tolerance (FIG. 5A, 1 week after). FIG. 5C depicts pictures of the adipose tissue which received a combination of the stapled peptides A and B labelled with FAM (green dots indicated with the white arrows). In FIG. 5D, the injection of the peptides in the adipose tissue of the Alms1foz/foz had no effect on systemic glycaemia for the simple reason that there is no active ALMS1 in the adipose tissue to be targeted by the peptide.

A variety of modified stapled peptides were designed to test the effect of modifying the peptide sequence on insulin-independent glucose uptake into adipocytes. Peptides were obtained from CPC Scientific.

Additional in vitro 2-deoxy-D-glucose-6-phosphate (DG6P) uptake results in human primary adipocytes for individual peptides of the present technology are provided in Tables 1-3.

TABLE 1.

| DG6P uptake results with peptides at 50 µM. | | | |
|---|---|---|---|
| | 2-DG6P (pmol) | 2-DG6P compared to −Insulin (%) | Peptide Sequence |
| −Insulin | 30.1 | 100.0 | |
| +Insulin | 94.2 | 312.6 | |
| AT001 50 µM | 44.2 | 146.8 | H-VECTM-R8-EKRVLA-S5-LDKPPFLTQLHS-OH (SEQ ID NO: 21) |
| AT003 50 µM | 46.2 | 153.3 | H-VECTM-R8-EKRVLA-S5-LDKPPFLTQLHS-NH$_2$ (Polypeptide) (SEQ ID NO: 22) |
| AT004 50 µM | 29.5 | 98.0 | Scrambled stapled peptide aggregating: |
| AT005 50 µM | 27.7 | 92.0 | H-LPHET-R8-RLSQKV-S5-TKLDCLMFVEPA-OH |
| AT006 50 µM | 30.7 | 102.0 | (SEQ ID NO: 36) |
| AT007 50 µM | 57.7 | 191.5 | H-VECTM-R8-EKRVLA-S5-LDKPPELTQLHS-OH (SEQ ID NO: 21) |
| AT008 50 µM | 53.3 | 177.0 | H-VECTM-S5-EKR-S5-LALLDKPPFLTQLHS-OH (SEQ ID NO: 35) |
| AT009 50 µM | 42.7 | 141.8 | H-CTM-R8-EKRVLA-S5-LDKPPFLTQLHS-OH (SEQ ID NO: 23) |
| AT010 50 µM | 35.7 | 118.6 | H-M-R8-EKRVLA-S5-LDKPPFLTQLHS-OH (SEQ ID NO: 24) |
| AT011 50 µM | 56.9 | 189.0 | Cbz-R8-EKRVLA-S5-LDKPPFLTQLHS-OH (SEQ ID NO: 25) |
| AT012 50 µM | 58.0 | 192.6 | H-VECTM-R8-EKRVLA-S5-LDKPPFLTQL-OH (SEQ ID NO: 26) |
| AT013 50 µM | 46.5 | 154.3 | H-VECTM-R8-EKRVLA-S5-LDKPPFLT-OH (SEQ ID NO: 27) |
| AT014 50 µM | 58.8 | 195.1 | H-VECTM-R8-EKRVLA-S5-LDKPPF-OH (SEQ ID NO: 28) |
| AT015 50 µM | 35.7 | 118.6 | H-VECTM-R8-EKRVEA-S5-EDKP-OH (SEQ ID NO: 29) |
| AT016 50 µM | 51.5 | 170.9 | H-VECTM-R8-EKRVEA-S5-ED-OH (SEQ ID NO: 30) |

TABLE 1.-continued

DG6P uptake results with peptides at 50 µM.

| | | 2-DG6P (pmol) | 2-DG6P compared to -Insulin (%) | Peptide Sequence |
|---|---|---|---|---|
| AT017 | 50 µM | 55.4 | 184.0 | H-VE(AAB)TM-R8-EKRVEA-S5-EDKPPFETQLHS-OH (SEQ ID NO: 31) |
| AT018 | 50 µM | 28.2 | 93.5 | H-VECT(AAH)-R8-EKRVLA-S5-LDKPPFLTQLHS-OH (SEQ ID NO: 32) |
| AT019 | 50 µM | 40.4 | 134.2 | H-VE(AAB)T(AAH)-R8-EKRVEA-S5-LDKPPELTQUIS-OH (SEQ ID NO: 33) |
| AT021 | 50 µM | 37.5 | 124.6 | H-VECTM-R8-EKRVLA-S5-LDKPPFLTQLHS-OH (SEQ ID NO: 21) |

TABLE 2

Dose response DG6P uptake results.

| | 2-DG6P (pmol) | 2-DG6P compared to -Insulin (%) | Peptide Sequence |
|---|---|---|---|
| -Ins | 21.8 | 100.0 | |
| +Ins | 79.3 | 363.3 | |
| AT001 0.001 µM | 19.9 | 91.2 | H-VECTM-R8-EKRVLA-S5-LDKPPFLTQLHS-OH (SEQ ID No: 21) |
| AT001 0.01 µM | 21.3 | 97.5 | |
| AT001 0.1 µM | 22.3 | 102.0 | |
| AT001 1 µM | 23.9 | 109.6 | |
| AT001 10 µM | 31.7 | 145.2 | |
| AT001 100 µM | 47.2 | 216.1 | |
| AT007 0.1 µM | 23.2 | 106.5 | H-VECTM-R8-EKRVLA-S5-LDKPPFLTQLHS-OH (SEQ ID NO: 21) |
| AT007 1 µM | 24.0 | 110.1 | |
| AT007 10 µM | 36.0 | 165.0 | |
| AT007 100 µM | 55.5 | 254.3 | |

TABLE 3

Dose response DG6P uptake results.

| | 2-DG6P (pmol) | 2-DG6P compared to -Insulin (%) | PeptideSequence |
|---|---|---|---|
| -Insulin | 13.7 | 100.0 | |
| +Insulin | 87.9 | 639.6 | |
| AT011 0.1 µM | 12.8 | 93.2 | Cbz-R8-EKRVLA-S5-LDKPPFLTQLHS-OH (SEQ ID NO: 25) |
| AT011 1 µM | 30.3 | 220.4 | |
| AT011 10 µM | 42.7 | 311.1 | |
| AT011 100 µM | 59.5 | 432.8 | |
| AT015 1 µM | 16.6 | 121.0 | H-VECTM-R8-EKRVLA-S5-LDKP-OH (SEQ ID NO: 29) |
| AT015 10 µM | 28.9 | 210.6 | |
| AT015 100 µM | 39.2 | 284.9 | |

TABLE 3-continued

Dose response DG6P uptake results.

| | 2-DG6P (pmol) | 2-DG6P compared to -Insulin (%) | PeptideSequence |
|---|---|---|---|
| AT016 1 µM | 23.7 | 172.4 | H-VECTM-R8-EKRVLA-S5-LD-OH (SEQ ID NO: 30) |
| AT016 10 µM | 38.6 | 280.6 | |
| AT016 100 µM | 51.4 | 373.7 | |

S5: (S)-2-(4-pentenyl)alanine
R8: (R)-2-(7-octenyl)alanine)
Cbz: Carboxybenzyle
AAB: alpha-aminobutyric acid (isostere of serine and cysteine)
AAH: alpha-aminoheptanoic acid (=homonorleucine, isostere of methionine)

These results demonstrate that the peptides of the present technology are useful in methods for stimulating cellular glucose uptake, such as in the treatment of diabetes mellitus Example 6: In-Silico Molecular Modelling of PATAD Peptide Variants and Molecular Docking Study with ALMS Protein This example demonstrates the use of in silico modelling to predict the binding of stapled peptides derived from the ALMS1 binding site of PKC when docked onto the PKC binding site on the ALMS1 protein.

Peptide Modelling: Peptides were modelled using the Build tool of UCSF Chimera and stapling was done using Avogadro software.

Energy Minimization: An extensive minimization and equilibration protocol was applied to all models to relax the peptides toward energetically favourable state and attain stability using UCSF Chimera software.

Molecular Docking: The docking analysis of ALMS protein with stapled and native peptides was carried out using HEX 8.0.0 docking software, which is an Interactive Molecular Graphics Program for calculating and displaying feasible docking modes of pairs of protein and peptide with lowest free energy. Parameters used for the docking process are listed in Table 4.

TABLE 4

Hex Docking Parameters

| Correlation Type | Shape + Electrostatistics |
|---|---|
| FFT Mode | 3D |
| Grid Dimensions | 1.0 |
| Receptor Range | 180 |
| Ligand Range | 180 |
| Twist Range | 360 |
| Distance Range | 40 |
| Solutions | 2000 |

The modelled peptides generated were docked with a structural model of ALMS1 protein using the above parameters. Visualization: Docked complexes were analysed and visualized to analyse the disparity between the initial and the docked state using Visual Molecular Dynamics Software. The modelled structure of the stapled peptides were also critically analysed as the stapling in the structure was thought likely to be crucial to peptide activity.

Results: All the modelled stapled and native peptides were energy minimized for 10,000 steps using steepest descent and conjugate gradient steps using AMBER ff99SB forcefield. All the energy minimized structures were saved in pdb format and further used for docking with a structural model of ALMS1 protein in HEX8.0.0 software.

Docking scores of ALMS1 protein with nonstapled and stapled peptides are shown in Table 5.

TABLE 5

Docking Scores

| Peptide | Stapled | Native |
|---|---|---|
| H-VECTM-R8-EKRVLA-S5-LDKPPFLTQLHS-OH (SEQ ID NO: 21) | -906.97 | -801.44 |
| H-VECTM-R8-EKRVLA-S5-LDKPPFLTQLHS-NH2 (SEQ ID NO: 22) | -830.79 | -920.83 |
| VECTMVEKRVLALLDKPPFLTQLHS (SEQ ID NO: 9) | -850.92 | |
| H-CTM-R8-EKRVLA-S5-LDKPPFLTQLHS-OH (SEQ ID NO: 23) | -825.37 | -843.97 |
| H-M-R8-EKRVLA-S5-LDKPPFLTQLHS-OH (SEQ ID NO: 24) | -876.45 | -867.45 |
| Cbz-R8-EKRVLA-S5-LDKPPFLTQLHS-OH (SEQ ID NO: 25) | -819.38 | -805.21 |
| H-VECTM-R8-EKRVLA-S5-LDKPPFLTQL-OH (SEQ ID NO: 26) | -866.33 | -839.42 |
| H-VECTM-R8-EKRVLA-S5-LDKPPFLT-OH (SEQ ID NO: 27) | -849.16 | -827.52 |
| H-VECTM-R8-EKRVLA-S5-LDKPPF-OH (SEQ ID NO: 28) | -783.16 | -730.93 |
| H-VECTM-R8-EKRVLA-S5-LDKP-OH (SEQ ID NO: 29) | -800.48 | -742.87 |
| H-VECTM-R8-EKRVLA-S5-LD-OH (SEQ ID NO: 30) | -739.21 | -860.67 |
| H-VE(AAB)TM-R8-EKRVLA-S5-LDKPPFLTQLHS-OH (SEQ ID NO: 31) | -825.00 | -812.45 |
| H-VECT(AAH)-R8-EKRVLA-S5-LDKPPFLTQLHS-OH (SEQ ID NO: 32) | -823.01 | -817.13 |
| H-VE(AAB)T(AAH)-R8-EKRVLA-S5-LDKPPFLTQLHS-OH (SEQ ID NO: 33) | -838.77 | -786.90 |
| H-VECTM-R8-EKRVLA-S5-LDKPPFLTQLHS-OH hydrogenated (SEQ NO: 34) | -764.89 | -759.55 |
| H-VECTM-S5-EKR-S5-LALLDKPPFLTQLHS-OH (SEQ ID NO: 35) | -881.59 | -815.50 |

The ranking of docking scores of native and stapled peptides show that the stapling can have a major effect on predicted binding to Alms1 Overall, the stapling increases the stability of the peptides making them more likely to bind ALMS1. Overall, the stapled peptides with highest homology to PKC had the best docking scores for ALMS1. The terminal OH or NH2 group on the peptide had an impact on the docking core, with a terminal hydroxyl group providing the highest docking score.

The invention claimed is:

1. A peptide that induces insulin-independent adipocyte glucose transport wherein
   the peptide has a length of at least 15 amino acids and less than 40 amino acids; and
   wherein the peptide sequence comprises a sequence selected from the group consisting of:

(SEQ ID NO: 9)
VECTMVEKRVLALLDKPPFLTQLHS;

(SEC) ID NO: 21)
H-VECTM-R8-EKRVLA-S5-LDKPPFLTQLHS-OH;

-continued (SEQ ID NO: 22)
H-VECTM-R8-EKRVLA-S5-LDKPPFLTQLHS-NH$_2$;

(SEQ ID NO: 23)
H-CTM-R8-EKRVLA-S5-LDKPPFLTQLHS-OH;

(SEQ ID NO: 24)
H-M-R8-EKRVLA-S5-LDKPPFLTQLHS-OH;

(SEQ ID NO: 25)
Cbz-R8-EKRVLA-S5-LDKPPFLTQLHS-OH;

(SEQ ID NO: 26)
H-VECTM-R8-EKRVLA-S5-LDKPPFLTQL-OH;

(SEQ ID NO: 27)
H-VECTM-R8-EKRVLA-S5-LDKPPFLT-OH;

(SEQ ID NO: 28)
H-VECTM-R8-EKRVLA-S5-LDKPPF-OH;

(SEQ ID NO: 29)
H-VECTM-R8-EKRVLA-S5-LDKP-OH;

(SEQ ID NO: 30)
H-VECTM-R8-EKRVLA-S5-LD-OH;

(SEQ ID NO: 31)
H-VE(AAB)TM-R8-EKRVLA-S5-LDKPPFLTQLHS-OH;
and (SEQ ID NO: 33)
H-VE(AAB)T(AAH)-R8-EKRVLA-S5-LDKPPFLTQLHS-OH.

2. The peptide according to claim 1, wherein the peptide is modified by a chemical cross-linking process.

3. The peptide according to claim 1, wherein the peptide sequence consists of:

(SEQ ID NO: 9)
VECTMVEKRVLALLDKPPFLTQLHS;

(SEQ ID NO: 21)
H-VECTM-R8-EKRVLA-S5-LDKPPFLTQLHS-OH;

(SEQ ID NO: 22)
H-VECTM-R8-EKRVLA-S5-LDKPPFLTQLHS-NH$_2$;

(SEQ ID NO: 23)
H-CTM-R8-EKRVLA-S5-LDKPPFLTQLHS-OH;

(SEQ ID NO: 24)
H-M-R8-EKRVLA-S5-LDKPPFLTQLHS-OH;

(SEQ ID NO: 25)
Cbz-R8-EKRVLA-S5-LDKPPFLTQLHS-OH;

(SEQ ID NO: 26)
H-VECTM-R8-EKRVLA-S5-LDKPPFLTQL-OH;

(SEQ ID NO: 27)
H-VECTM-R8-EKRVLA-S5-LDKPPFLT-OH;

(SEQ ID NO: 28)
H-VECTM-R8-EKRVLA-S5-LDKPPF-OH;

(SEQ ID NO: 29)
H-VECTM-R8-EKRVLA-S5-LDKP-OH;

(SEQ ID NO: 30)
H-VECTM-R8-EKRVLA-S5-LD-OH;

(SEQ ID NO: 31)
H-VE(AAB)TM-R8-EKRVLA-S5-LDKPPFLTQLHS-OH;
or (SEQ ID NO: 33)
H-VE(AAB)T(AAH)-R8-EKRVLA-S5-LDKPPFLTQLHS-OH.

4. The peptide according to claim 1, wherein the peptide has a hydroxyl end group.

5. A pharmaceutical composition comprising a peptide according to claim 1.

6. The pharmaceutical composition according to claim 5, said composition further comprising an anti-diabetic agent selected from the group consisting of insulin, metformin, sulfonylurea, alpha-glucosidase inhibitors, thiazolidinediones, meglitinide, incretin mimetic, glucagon-like peptide analog, dipeptidyl peptidase-4 inhibitor, amylin analog, sodium glucose transporter inhibitor, and any combination thereof.

* * * * *

UNITED STATES PATENT AND TRADEMARK OFFICE
CERTIFICATE OF CORRECTION

PATENT NO. : 11,332,503 B2
APPLICATION NO. : 16/627389
DATED : May 17, 2022
INVENTOR(S) : Vincent Marion and Nikolai Petrovsky It is certified that error appears in the above-identified patent and that said Letters Patent is hereby corrected as shown below:

In the Specification

Column 3,
Line 34, "VECTMVEKRVLALLDKPPFLTQLHS" should read
--VECTM<u>V</u>EKRVLA<u>L</u>LDKPPFLTQLHS--.
Line 35, "MCKEHMMDGVTTRTFCGTPD" should read
--MC<u>K</u>EHMMDG<u>V</u>TTRTFCGTPD--.
Line 36, "SICKGLMTKHPAKRLGCGPEG" should read
--S<u>I</u>CKGLMT<u>K</u>HPAKRLGCGPEG--.

Column 4,
Line 8, "NH2" should read --NH$_2$--.

Column 11,
Line 48, "5562, 5566," should read --S562, S566,--.
Line 50, "5562, 5567," should read --S562, S567,--.

Column 26,
Lines 63-64, "H-VECTM-R8-EKRVEA-S5-EDKP-OH (SEQ ID NO: 29)" should read --H-VECTM-R8-EKRVLA-S5-LDKP-OH (SEQ ID NO: 29)--.
Lines 66-67, "H-VECTM-R8-EKRVEA-S5-ED-011 (SEQ ID NO: 30)" should read --H-VECTM-R8-EKRVLA-S5-LD-OH (SEQ ID NO: 30)--.

Column 27,
Lines 8-9, "H-VE(AAB)TM-R8-EKRVEA-S5-EDKPPFETQLHS-OH (SEQ ID NO: 31)" should read --H-VE(AAB)TM-R8-EKRVLA-S5-LDKPPFLTQLHS-OH (SEQ ID NO: 31)--.

Signed and Sealed this
Eighteenth Day of April, 2023

Katherine Kelly Vidal
*Director of the United States Patent and Trademark Office*

Column 27,
Lines 12-14, "H-VE(AAB)T(AAH)-R8-EKRVEA-S5-LDKPPELTQUIS-OH (SEQ ID NO: 33)" should read --H-VE(AAB)T(AAH)-R8-EKRVLA-S5-LDKPPFLTQLHS-OH (SEQ ID NO: 33)--.
Line 55, "PeptideSequence" should read --Peptide Sequence--.

Column 30,
Line 39, "Alms1 Overall," should read --Alms1. Overall,--.

SEQUENCE LISTING

```
<160> NUMBER OF SEQ ID NOS: 37

<210> SEQ ID NO 1
<211> LENGTH: 672
<212> TYPE: PRT
<213> ORGANISM: Homo sapiens

<400> SEQUENCE: 1

Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
            20                  25                  30

Glu Val Lys Asp His Lys Phe Ile Ala Arg Phe Phe Lys Gln Pro Thr
        35                  40                  45

Phe Cys Ser His Cys Thr Asp Phe Ile Trp Gly Phe Gly Lys Gln Gly
    50                  55                  60
```

```
Phe Gln Cys Gln Val Cys Cys Phe Val Val His Lys Arg Cys His Glu
 65                  70                  75                  80

Phe Val Thr Phe Ser Cys Pro Gly Ala Asp Lys Gly Pro Asp Thr Asp
                 85                  90                  95

Asp Pro Arg Ser Lys His Lys Phe Lys Ile His Thr Tyr Gly Ser Pro
                100                 105                 110

Thr Phe Cys Asp His Cys Gly Ser Leu Leu Tyr Gly Leu Ile His Gln
            115                 120                 125

Gly Met Lys Cys Asp Thr Cys Asp Met Asn Val His Lys Gln Cys Val
        130                 135                 140

Ile Asn Val Pro Ser Leu Cys Gly Met Asp His Thr Glu Lys Arg Gly
145                 150                 155                 160

Arg Ile Tyr Leu Lys Ala Glu Val Ala Asp Glu Lys Leu His Val Thr
                165                 170                 175

Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
        195                 200                 205

Lys Gln Lys Thr Lys Thr Ile Arg Ser Thr Leu Asn Pro Gln Trp Asn
210                 215                 220

Glu Ser Phe Thr Phe Lys Leu Lys Pro Ser Asp Lys Asp Arg Arg Leu
225                 230                 235                 240

Ser Val Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
            260                 265                 270

Gly Trp Tyr Lys Leu Leu Asn Gln Glu Glu Gly Glu Tyr Tyr Asn Val
        275                 280                 285

Pro Ile Pro Glu Gly Asp Glu Glu Gly Asn Met Glu Leu Arg Gln Lys
    290                 295                 300

Phe Glu Lys Ala Lys Leu Gly Pro Ala Gly Asn Lys Val Ile Ser Pro
305                 310                 315                 320

Ser Glu Asp Arg Lys Gln Pro Ser Asn Asn Leu Asp Arg Val Lys Leu
                325                 330                 335

Thr Asp Phe Asn Phe Leu Met Val Leu Gly Lys Gly Ser Phe Gly Lys
            340                 345                 350

Val Met Leu Ala Asp Arg Lys Gly Thr Glu Glu Leu Tyr Ala Ile Lys
        355                 360                 365

Ile Leu Lys Lys Asp Val Val Ile Gln Asp Asp Val Glu Cys Thr
370                 375                 380

Met Val Glu Lys Arg Val Leu Ala Leu Leu Asp Lys Pro Pro Phe Leu
385                 390                 395                 400

Thr Gln Leu His Ser Cys Phe Gln Thr Val Asp Arg Leu Tyr Phe Val
                405                 410                 415

Met Glu Tyr Val Asn Gly Gly Asp Leu Met Tyr His Ile Gln Gln Val
            420                 425                 430

Gly Lys Phe Lys Glu Pro Gln Ala Val Phe Tyr Ala Ala Glu Ile Ser
        435                 440                 445

Ile Gly Leu Phe Phe Leu His Lys Arg Gly Ile Ile Tyr Arg Asp Leu
    450                 455                 460

Lys Leu Asp Asn Val Met Leu Asp Ser Glu Gly His Ile Lys Ile Ala
465                 470                 475                 480

Asp Phe Gly Met Cys Lys Glu His Met Met Asp Gly Val Thr Thr Arg
```

```
                    485                 490                 495
Thr Phe Cys Gly Thr Pro Asp Tyr Ile Ala Pro Glu Ile Ile Ala Tyr
            500                 505                 510

Gln Pro Tyr Gly Lys Ser Val Asp Trp Trp Ala Tyr Gly Val Leu Leu
        515                 520                 525

Tyr Glu Met Leu Ala Gly Gln Pro Pro Phe Asp Gly Glu Asp Glu Asp
    530                 535                 540

Glu Leu Phe Gln Ser Ile Met Glu His Asn Val Ser Tyr Pro Lys Ser
545                 550                 555                 560

Leu Ser Lys Glu Ala Val Ser Ile Cys Lys Gly Leu Met Thr Lys His
                565                 570                 575

Pro Ala Lys Arg Leu Gly Cys Gly Pro Glu Gly Glu Arg Asp Val Arg
            580                 585                 590

Glu His Ala Phe Phe Arg Arg Ile Asp Trp Glu Lys Leu Glu Asn Arg
        595                 600                 605

Glu Ile Gln Pro Pro Phe Lys Pro Lys Val Cys Gly Lys Gly Ala Glu
    610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
                645                 650                 655

Ser Tyr Val Asn Pro Gln Phe Val His Pro Ile Leu Gln Ser Ala Val
            660                 665                 670

<210> SEQ ID NO 2
<211> LENGTH: 13
<212> TYPE: PRT
<213> ORGANISM: Homo sapiens

<400> SEQUENCE: 2

Met Val Glu Lys Arg Val Leu Ala Leu Leu Asp Lys Pro
1               5                   10

<210> SEQ ID NO 3
<211> LENGTH: 20
<212> TYPE: PRT
<213> ORGANISM: Homo sapiens

<400> SEQUENCE: 3

Pro Phe Leu Thr Gln Leu His Ser Cys Phe Gln Thr Val Asp Arg Leu
1               5                   10                  15

Tyr Phe Val Met
            20

<210> SEQ ID NO 4
<211> LENGTH: 27
<212> TYPE: PRT
<213> ORGANISM: Homo sapiens

<400> SEQUENCE: 4

Arg Leu Tyr Phe Val Met Glu Tyr Val Asn Gly Gly Asp Leu Met Tyr
1               5                   10                  15

His Ile Gln Gln Val Gly Lys Phe Lys Glu Pro
            20                  25

<210> SEQ ID NO 5
<211> LENGTH: 32
<212> TYPE: PRT
<213> ORGANISM: Homo sapiens
```

```
<400> SEQUENCE: 5

Met Tyr His Ile Gln Gln Val Gly Lys Phe Lys Glu Pro Gln Ala Val
1               5                   10                  15

Phe Tyr Ala Ala Glu Ile Ser Ile Gly Leu Phe Phe Leu His Lys Arg
            20                  25                  30

<210> SEQ ID NO 6
<211> LENGTH: 33
<212> TYPE: PRT
<213> ORGANISM: Homo sapiens

<400> SEQUENCE: 6

Pro Gln Ala Val Phe Tyr Ala Ala Glu Ile Ser Ile Gly Leu Phe Phe
1               5                   10                  15

Leu His Lys Arg Gly Ile Ile Tyr Arg Asp Leu Lys Leu Asp Asn Val
            20                  25                  30

Met

<210> SEQ ID NO 7
<211> LENGTH: 13
<212> TYPE: PRT
<213> ORGANISM: Homo sapiens

<400> SEQUENCE: 7

Met Asp Gly Val Thr Thr Arg Thr Phe Cys Gly Thr Pro
1               5                   10

<210> SEQ ID NO 8
<211> LENGTH: 8
<212> TYPE: PRT
<213> ORGANISM: Homo sapiens

<400> SEQUENCE: 8

Met Thr Lys His Pro Ala Lys Arg
1               5

<210> SEQ ID NO 9
<211> LENGTH: 25
<212> TYPE: PRT
<213> ORGANISM: Homo sapiens

<400> SEQUENCE: 9

Val Glu Cys Thr Met Val Glu Lys Arg Val Leu Ala Leu Leu Asp Lys
1               5                   10                  15

Pro Pro Phe Leu Thr Gln Leu His Ser
            20                  25

<210> SEQ ID NO 10
<211> LENGTH: 20
<212> TYPE: PRT
<213> ORGANISM: Homo sapiens

<400> SEQUENCE: 10

Met Cys Lys Glu His Met Met Asp Gly Val Thr Thr Arg Thr Phe Cys
1               5                   10                  15

Gly Thr Pro Asp
            20

<210> SEQ ID NO 11
<211> LENGTH: 21
<212> TYPE: PRT
```

-continued

<213> ORGANISM: Homo sapiens

<400> SEQUENCE: 11

Ser Ile Cys Lys Gly Leu Met Thr Lys His Pro Ala Lys Arg Leu Gly
1               5                   10                  15

Cys Gly Pro Glu Gly
            20

<210> SEQ ID NO 12
<211> LENGTH: 40
<212> TYPE: PRT
<213> ORGANISM: Homo sapiens

<400> SEQUENCE: 12

Arg Lys Gly Thr Glu Glu Leu Tyr Ala Ile Lys Ile Leu Lys Lys Asp
1               5                   10                  15

Val Val Ile Gln Asp Asp Asp Val Glu Cys Thr Met Val Glu Lys Arg
            20                  25                  30

Val Leu Ala Leu Leu Asp Lys Pro
        35                  40

<210> SEQ ID NO 13
<211> LENGTH: 29
<212> TYPE: PRT
<213> ORGANISM: Homo sapiens

<400> SEQUENCE: 13

Arg Val Leu Ala Leu Leu Asp Lys Pro Pro Phe Leu Thr Gln Leu His
1               5                   10                  15

Ser Cys Phe Gln Thr Val Asp Arg Leu Tyr Phe Val Met
            20                  25

<210> SEQ ID NO 14
<211> LENGTH: 36
<212> TYPE: PRT
<213> ORGANISM: Homo sapiens

<400> SEQUENCE: 14

Arg Thr Phe Cys Gly Thr Pro Asp Tyr Ile Ala Pro Glu Ile Ile Ala
1               5                   10                  15

Tyr Gln Pro Tyr Gly Lys Ser Val Asp Trp Trp Ala Tyr Gly Val Leu
            20                  25                  30

Leu Tyr Glu Met
        35

<210> SEQ ID NO 15
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic PTD R8 peptide"

<400> SEQUENCE: 15

Arg Arg Arg Arg Arg Arg Arg Arg
1               5

<210> SEQ ID NO 16
<211> LENGTH: 15
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic PTD peptide"

<400> SEQUENCE: 16

Arg Arg Pro Arg Arg Pro Arg Arg Pro Arg Arg Pro Arg Arg Pro
1               5                   10                  15

<210> SEQ ID NO 17
<211> LENGTH: 16
<212> TYPE: PRT
<213> ORGANISM: Drosophila sp.

<400> SEQUENCE: 17

Arg Gln Ile Lys Ile Trp Phe Gln Asn Arg Arg Met Lys Trp Lys Lys
1               5                   10                  15

<210> SEQ ID NO 18
<211> LENGTH: 11
<212> TYPE: PRT
<213> ORGANISM: Human immunodeficiency virus

<400> SEQUENCE: 18

Tyr Gly Arg Lys Lys Arg Arg Gln Arg Arg Arg
1               5                   10

<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19 acaactttc atggctccag t                                          21

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
ttggctcaga gacagttgaa a                                         21

<210> SEQ ID NO 21
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 21
```

```
Val Glu Cys Thr Met Xaa Glu Lys Arg Val Leu Ala Xaa Leu Asp Lys
1               5                   10                  15

Pro Pro Phe Leu Thr Gln Leu His Ser
            20                  25

<210> SEQ ID NO 22
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 22

Val Glu Cys Thr Met Xaa Glu Lys Arg Val Leu Ala Xaa Leu Asp Lys
1               5                   10                  15

Pro Pro Phe Leu Thr Gln Leu His Ser
            20                  25

<210> SEQ ID NO 23
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: (R)-2-(7-octenyl)alanine
<220> FEATURE:
<221> NAME/KEY: MOD_RES
<222> LOCATION: (11)..(11)
<223> OTHER INFORMATION: (S)-2-(4-pentenyl)alanine

<400> SEQUENCE: 23

Cys Thr Met Xaa Glu Lys Arg Val Leu Ala Xaa Leu Asp Lys Pro Pro
1               5                   10                  15

Phe Leu Thr Gln Leu His Ser
            20

<210> SEQ ID NO 24
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (R)-2-(7-octenyl)alanine
<220> FEATURE:
<221> NAME/KEY: MOD_RES
<222> LOCATION: (9)..(9)
<223> OTHER INFORMATION: (S)-2-(4-pentenyl)alanine

<400> SEQUENCE: 24

Met Xaa Glu Lys Arg Val Leu Ala Xaa Leu Asp Lys Pro Pro Phe Leu
```

```
1               5                   10                  15

Thr Gln Leu His Ser
            20

<210> SEQ ID NO 25
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term carboxybenzyle"
<220> FEATURE:
<221> NAME/KEY: MOD_RES
<222> LOCATION: (1)..(1)
<223> OTHER INFORMATION: (R)-2-(7-octenyl)alanine
<220> FEATURE:
<221> NAME/KEY: MOD_RES
<222> LOCATION: (8)..(8)
<223> OTHER INFORMATION: (S)-2-(4-pentenyl)alanine

<400> SEQUENCE: 25

Xaa Glu Lys Arg Val Leu Ala Xaa Leu Asp Lys Pro Pro Phe Leu Thr
1               5                   10                  15

Gln Leu His Ser
            20

<210> SEQ ID NO 26
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 26

Val Glu Cys Thr Met Xaa Glu Lys Arg Val Leu Ala Xaa Leu Asp Lys
1               5                   10                  15

Pro Pro Phe Leu Thr Gln Leu
            20

<210> SEQ ID NO 27
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 27
```

-continued

```
Val Glu Cys Thr Met Xaa Glu Lys Arg Val Leu Ala Xaa Leu Asp Lys
1               5                   10                  15

Pro Pro Phe Leu Thr
            20

<210> SEQ ID NO 28
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 28

Val Glu Cys Thr Met Xaa Glu Lys Arg Val Leu Ala Xaa Leu Asp Lys
1               5                   10                  15

Pro Pro Phe

<210> SEQ ID NO 29
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 29

Val Glu Cys Thr Met Xaa Glu Lys Arg Val Leu Ala Xaa Leu Asp Lys
1               5                   10                  15

Pro

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 30

Val Glu Cys Thr Met Xaa Glu Lys Arg Val Leu Ala Xaa Leu Asp
1               5                   10                  15
```

```
<210> SEQ ID NO 31
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Alpha-aminobutyric acid
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 31

Val Glu Xaa Thr Met Xaa Glu Lys Arg Val Leu Ala Xaa Leu Asp Lys
1               5                   10                  15

Pro Pro Phe Leu Thr Gln Leu His Ser
            20                  25

<210> SEQ ID NO 32
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Alpha-aminoheptanoic acid
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 32

Val Glu Cys Thr Xaa Xaa Glu Lys Arg Val Leu Ala Xaa Leu Asp Lys
1               5                   10                  15

Pro Pro Phe Leu Thr Gln Leu His Ser
            20                  25

<210> SEQ ID NO 33
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Alpha-aminobutyric acid
<220> FEATURE:
<221> NAME/KEY: MOD_RES
<222> LOCATION: (5)..(5)
<223> OTHER INFORMATION: Alpha-aminoheptanoic acid
<220> FEATURE:
```

```
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 33

Val Glu Xaa Thr Xaa Xaa Glu Lys Arg Val Leu Ala Xaa Leu Asp Lys
1               5                   10                  15

Pro Pro Phe Leu Thr Gln Leu His Ser
            20                  25

<210> SEQ ID NO 34
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 34

Val Glu Cys Thr Met Xaa Glu Lys Arg Val Leu Ala Xaa Leu Asp Lys
1               5                   10                  15

Pro Pro Phe Leu Thr Gln Leu His Ser
            20                  25

<210> SEQ ID NO 35
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (S)-2-(4-pentenyl)alanine
<220> FEATURE:
<221> NAME/KEY: MOD_RES
<222> LOCATION: (10)..(10)
<223> OTHER INFORMATION: (S)-2-(4-pentenyl)alanine

<400> SEQUENCE: 35

Val Glu Cys Thr Met Xaa Glu Lys Arg Xaa Leu Ala Leu Leu Asp Lys
1               5                   10                  15

Pro Pro Phe Leu Thr Gln Leu His Ser
            20                  25

<210> SEQ ID NO 36
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (6)..(6)
<223> OTHER INFORMATION: (R)-2-(7-octenyl)alanine
<220> FEATURE:
<221> NAME/KEY: MOD_RES
<222> LOCATION: (13)..(13)
<223> OTHER INFORMATION: (S)-2-(4-pentenyl)alanine

<400> SEQUENCE: 36

Leu Pro His Glu Thr Xaa Arg Leu Ser Gln Lys Val Xaa Thr Lys Leu
1               5                   10                  15

Asp Cys Leu Met Phe Val Glu Pro Ala
            20                  25

<210> SEQ ID NO 37
<211> LENGTH: 672
<212> TYPE: PRT
<213> ORGANISM: Homo sapiens

<400> SEQUENCE: 37

Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
            20                  25                  30

Glu Val Lys Asp His Lys Phe Ile Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Asp Met Asn Val His Lys Gln Cys Val
    130                 135                 140

Ile Asn Val Pro Ser Leu Cys Gly Met Asp His Thr Glu Lys Arg Gly
145                 150                 155                 160

Arg Ile Tyr Leu Lys Ala Glu Val Ala Asp Glu Lys Leu His Val Thr
                165                 170                 175

Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
        195                 200                 205

Lys Gln Lys Thr Lys Thr Ile Arg Ser Thr Leu Asn Pro Gln Trp Asn
    210                 215                 220

Glu Ser Phe Thr Phe Lys Leu Lys Pro Ser Asp Lys Asp Arg Arg Leu
225                 230                 235                 240

Ser Val Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
            260                 265                 270

Gly Trp Tyr Lys Leu Leu Asn Gln Glu Glu Gly Glu Tyr Tyr Asn Val
        275                 280                 285

Pro Ile Pro Glu Gly Asp Glu Glu Gly Asn Met Glu Leu Arg Gln Lys
    290                 295                 300
```

```
Phe Glu Lys Ala Lys Leu Gly Pro Ala Gly Asn Lys Val Ile Ser Pro
305                 310                 315                 320

Ser Glu Asp Arg Lys Gln Pro Ser Asn Asn Leu Asp Arg Val Lys Leu
                325                 330                 335

Thr Asp Phe Asn Phe Leu Met Val Leu Gly Lys Gly Ser Phe Gly Lys
                340                 345                 350

Val Met Leu Ala Asp Arg Lys Gly Thr Glu Glu Leu Tyr Ala Ile Lys
                355                 360                 365

Ile Leu Lys Lys Asp Val Val Ile Gln Asp Asp Val Glu Cys Thr
370                 375                 380

Met Val Glu Lys Arg Val Leu Ala Leu Leu Asp Lys Pro Pro Phe Leu
385                 390                 395                 400

Thr Gln Leu His Ser Cys Phe Gln Thr Val Asp Arg Leu Tyr Phe Val
                405                 410                 415

Met Glu Tyr Val Asn Gly Gly Asp Leu Met Tyr His Ile Gln Gln Val
                420                 425                 430

Gly Lys Phe Lys Glu Pro Gln Ala Val Phe Tyr Ala Ala Glu Ile Ser
                435                 440                 445

Ile Gly Leu Phe Phe Leu His Lys Arg Gly Ile Ile Tyr Arg Asp Leu
450                 455                 460

Lys Leu Asp Asn Val Met Leu Asp Ser Glu Gly His Ile Lys Ile Ala
465                 470                 475                 480

Asp Phe Gly Met Cys Lys Glu His Met Met Asp Gly Val Thr Thr Arg
                485                 490                 495

Thr Phe Cys Gly Thr Pro Asp Tyr Ile Ala Pro Glu Ile Ile Ala Tyr
                500                 505                 510

Gln Pro Tyr Gly Lys Ser Val Asp Trp Trp Ala Tyr Gly Val Leu Leu
                515                 520                 525

Tyr Glu Met Leu Ala Gly Gln Pro Pro Phe Asp Gly Glu Asp Glu Asp
530                 535                 540

Glu Leu Phe Gln Ser Ile Met Glu His Asn Val Ser Tyr Pro Lys Ser
545                 550                 555                 560

Leu Ser Lys Glu Ala Val Ser Val Cys Lys Gly Leu Met Thr Lys His
                565                 570                 575

Pro Ala Lys Arg Leu Gly Cys Gly Pro Glu Gly Glu Arg Asp Val Arg
                580                 585                 590

Glu His Ala Phe Phe Arg Arg Ile Asp Trp Glu Lys Leu Glu Asn Arg
                595                 600                 605

Glu Ile Gln Pro Pro Phe Lys Pro Lys Val Cys Gly Lys Gly Ala Glu
                610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
                645                 650                 655

Ser Tyr Val Asn Pro Gln Phe Val His Pro Ile Leu Gln Ser Ala Val
                660                 665                 670
```